United States Patent
Stewart et al.

(10) Patent No.: US 10,099,178 B2
(45) Date of Patent: Oct. 16, 2018

(54) DRAW SOLUTIONS AND METHODS OF TREATING AN AQUEOUS LIQUID

(71) Applicant: BATTELLE ENERGY ALLIANCE, LLC, Idaho Falls, ID (US)

(72) Inventors: Frederick F. Stewart, Idaho Falls, ID (US); Michael T. Benson, Idaho Falls, ID (US); Mark L. Stone, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 417 days.

(21) Appl. No.: 14/948,019

(22) Filed: Nov. 20, 2015

(65) Prior Publication Data

US 2016/0074811 A1 Mar. 17, 2016

Related U.S. Application Data

(63) Continuation of application No. 13/479,726, filed on May 24, 2012, now abandoned.
(Continued)

(51) Int. Cl.
*B01D 61/00* (2006.01)
*C07D 251/70* (2006.01)
(Continued)

(52) U.S. Cl.
CPC ......... *B01D 61/005* (2013.01); *B01D 61/007* (2013.01); *C02F 1/445* (2013.01);
(Continued)

(58) Field of Classification Search
CPC combination set(s) only.
See application file for complete search history.

(56) References Cited

U.S. PATENT DOCUMENTS 4,405,738 A * 9/1983 McNeely ............. C08K 5/5399
524/116
4,440,921 A 4/1984 Allcock et al.
(Continued)

OTHER PUBLICATIONS

Allcock et al., "An Ionically Cross-Linkable Polyphosphazene: Poly[bis(carboxylatophenoxy)phosphazene] and Its Hydrogels and Membranes," Macromolecules 1989, 22, 75-79.
(Continued)

*Primary Examiner* — Krishnan S Menon
*Assistant Examiner* — Ryan B Huang
(74) *Attorney, Agent, or Firm* — TraskBritt

(57) ABSTRACT

A method of treating an aqueous liquid. The method comprises providing an aqueous feed liquid comprising water and at least one solute to a first side of a membrane. A draw solution comprising water and a draw solute comprising at least one of a phosphazene compound and a triazine compound is provided to a second side of the membrane. At least a portion of the water of the aqueous feed liquid is osmosed across the membrane and into the draw solution to form a diluted draw solution comprising water and the draw solute. The water of the diluted draw solution is separated from the draw solute of the diluted draw solution to form a purified water product. Draw solutes comprising phosphazene compounds and draw solutes comprising triazine compounds are also disclosed, as are methods of forming the draw solutes.

13 Claims, 6 Drawing Sheets

Related U.S. Application Data

(60) Provisional application No. 61/527,936, filed on Aug. 26, 2011.

(51) Int. Cl.

| | |
|---|---|
| *C02F 1/44* | (2006.01) |
| *C07F 9/6593* | (2006.01) |
| *C07D 251/54* | (2006.01) |
| *C02F 103/08* | (2006.01) |

(52) U.S. Cl.
CPC ......... *C07D 251/54* (2013.01); *C07D 251/70* (2013.01); *C07F 9/65815* (2013.01); *C02F 2103/08* (2013.01)

(56) References Cited

U.S. PATENT DOCUMENTS

| | | | |
|---|---|---|---|
| 5,994,497 | A | 11/1999 | Raith et al. |
| 7,099,142 | B2 | 8/2006 | Otsuki et al. |
| 7,560,029 | B2 | 7/2009 | McGinnis |
| 2005/0145568 | A1 | 7/2005 | McGinnis |
| 2006/0144789 | A1 | 7/2006 | Cath et al. |
| 2009/0308727 | A1 | 12/2009 | Kirts |
| 2010/0155329 | A1 | 6/2010 | Iyer |
| 2010/0213129 | A1 | 8/2010 | Jones et al. |

OTHER PUBLICATIONS

Allcock, H. "The Synthesis of Functional Polyphosphazenes and their Surfaces," Applied Organometallic Chemistry, 12 (1998), 659-666, 8 pages.

Liu et al., "Current Patents of Forward Osmosis Membrane Process," Recent Patents on Chemical Engineering, 2009, 2, 76-82.

Oike et al., "Designing Unusual Polymer Topologies by Electrostatic Self-Assembly and Covant Fixation," J Am Chem Soc, 122 (2000), 9592-9599, 8 pages.

Stewart et al., "Synthesis and Characterization of Esterified Poly[(aryloxy)phosphazene]s," Macromolecules 1997, 30, 3229-3233.

Yen et al., "Study of draw solutes using 2-methylimidazole-based compounds in forward osmosis," Journal of Membrane Science 364 (2010) 242-252.

\* cited by examiner

DRAW SOLUTIONS AND METHODS OF TREATING AN AQUEOUS LIQUID

CROSS-REFERENCE TO RELATED APPLICATIONS

This application is a continuation of U.S. patent application Ser. No. 13/479,726, filed May 24, 2012 now abandoned, which claims the benefit of U.S. Provisional Patent Application Ser. No. 61/527,936, filed Aug. 26, 2011, the disclosure of each of which is hereby incorporated herein in its entirety by this reference.

STATEMENT REGARDING FEDERALLY SPONSORED RESEARCH OR DEVELOPMENT

This invention was made with government support under Contract Number DE-AC07-05ID14517 awarded by the United States Department of Energy. The government has certain rights in the invention.

TECHNICAL FIELD

The present disclosure, in various embodiments, relates generally to draw solutes for use in treating an aqueous liquid, to methods of forming such draw solutes, and to related methods of treating an aqueous liquid to purify or concentrate at least one of water and a solute therein. More specifically, embodiments of the present disclosure relate to phosphazene compounds and triazine compounds for use as draw solutes, to methods of forming such phosphazene compounds and such triazine compounds, and to methods of treating an aqueous liquid using such phosphazene compounds and such triazine compounds.

BACKGROUND

Decreasing water supplies throughout much of the industrialized world necessitate new methods and systems for utilizing water including contaminants and impurities. Additionally, certain industries have a need for safer, more energy efficient methods and systems for removing water from a target material or solute. Conventional methods and systems of aqueous liquid treatment include thermal flash evaporation and membrane filtration. The most popular membrane filtration method is reverse osmosis, in which water is separated from solutes (e.g., contaminants) in an aqueous feed liquid by application of a pressure overcoming the osmotic pressure of the aqueous feed liquid. For water desalination processes, the pressure to overcome the osmotic pressure of the contaminated water source can be substantial, such as greater than 50 atm, significant investment in equipment and substantial ongoing energy costs. Additionally, the application of pressure in reverse osmosis processes often exacerbates membrane fouling by inorganic and organic molecules.

Forward osmosis circumvents several of the deficiencies of reverse osmosis by using osmotic pressure gradients across a semi-permeable membrane to diffuse water from the aqueous feed liquid into a draw solution. The draw solution includes a draw solute that enables the draw solution to have a greater osmotic pressure than the aqueous feed liquid. Conventional draw solutes include sodium chloride, potassium chloride, magnesium chloride, calcium chloride, sulfur dioxide, magnesium sulfate, aluminum sulfate, sugars (e.g., glucose, fructose, sucrose), potassium nitrate, ammonium carbonate, and ammonium carbamate.

Unfortunately, the molecular weight and size of conventional draw solutes frequently results in back diffusion of the draw solute through the semi-permeable membrane, requiring added expense to replace the draw solute that is lost. The molecular weight and size of conventional draw solutes also typically requires costly and energy intensive processes, such as reverse osmosis, to remove the conventional draw solutes from the water they draw. Further, conventional draw solutes are generally non-ionic, monovalent, or divalent, meaning that the osmotic pressure they impart can be limited, as can be the flux of water through the semi-permeable membrane during forward osmosis.

It would, therefore, be desirable to have a relatively larger draw solute that does not back-diffuse through the semi-permeable membrane, and that may be removed from the water it draws by relatively less expensive separation processes. It would also be desirable for the draw solute to have relatively increased durability, and increased osmotic pressure as compared to conventional draw solutes. The use of such a draw solute would reduce the energy demands and operational costs associated with current water treatment technologies, including a broad array of operations such as bulk water purification, produced water (e.g., waters brought to the surface during oil and gas drilling) utilization, solution mining (e.g., mining of underground, water-soluble minerals), carbon dioxide scrubbing, and acid gas scrubbing.

BRIEF SUMMARY

Embodiments described herein include draw solutes, methods of forming draw solutes, and methods of treating an aqueous liquid to purify or concentrate at least one of water and a solute therein. In accordance with one embodiment described herein, a draw solute comprises at least one phosphazene compound comprising the following chemical structure:

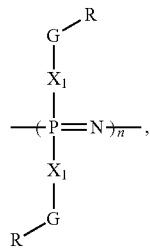

where each $X_1$ independently comprises —O—, —S—, or —NH—; each G independently comprises an alkylene group, an alkenylene group, an alkynylene group, an alicyclic group, an arylene group —CO—, —SO$_2$—, —SO—, —PO—, —O—, —S—, and —NH—; each R independently comprises a salt functional group; and n comprises an integer of from 3 to 5.

In additional embodiments, a draw solute comprises at least one triazine compound comprising the following chemical structure:

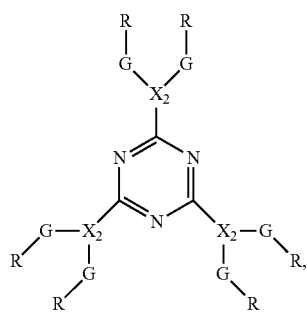

where each $X_2$ independently comprises —N—, —P—, —CH—, or —SiH—; each G independently comprises an alkylene group, an alkenylene group, an alkynylene group, an alicyclic group, an arylene group, —CO—, —SO$_2$—, —SO—, —PO—, —O—, —S—, and —NH—; and each R independently comprises a salt functional group.

In yet additional embodiments, a method of treating an aqueous liquid comprises providing an aqueous feed liquid comprising water and at least one solute to a first side of a membrane. A draw solution comprising water and a draw solute comprising at least one of a phosphazene compound and a triazine compound is provided to a second side of the membrane. At least a portion of the water of the aqueous feed liquid is osmosed across the membrane and into the draw solution to form a diluted draw solution comprising water and the draw solute. The water of the diluted draw solution is separated from the draw solute of the of diluted draw solution to form a purified water product.

In yet still additional embodiments, a method of forming a draw solute comprises reacting a halogenated phosphazene compound with a nucleophilic compound to form a fully-substituted phosphazene compound. The fully-substituted phosphazene compound is hydrolyzed to form an acidic phosphazene compound comprising acid-terminated pendant groups. The acidic phosphazene compound is neutralized to form a phosphazene compound comprising salt-terminated pendant groups.

BRIEF DESCRIPTION OF THE SEVERAL VIEWS OF THE DRAWINGS

While the specification concludes with claims particularly pointing out and distinctly claiming that which is regarded as the invention, advantages of the invention can be more readily ascertained from the following detailed description when read in conjunction with the accompanying drawings in which:

DETAILED DESCRIPTION

Figure 1:
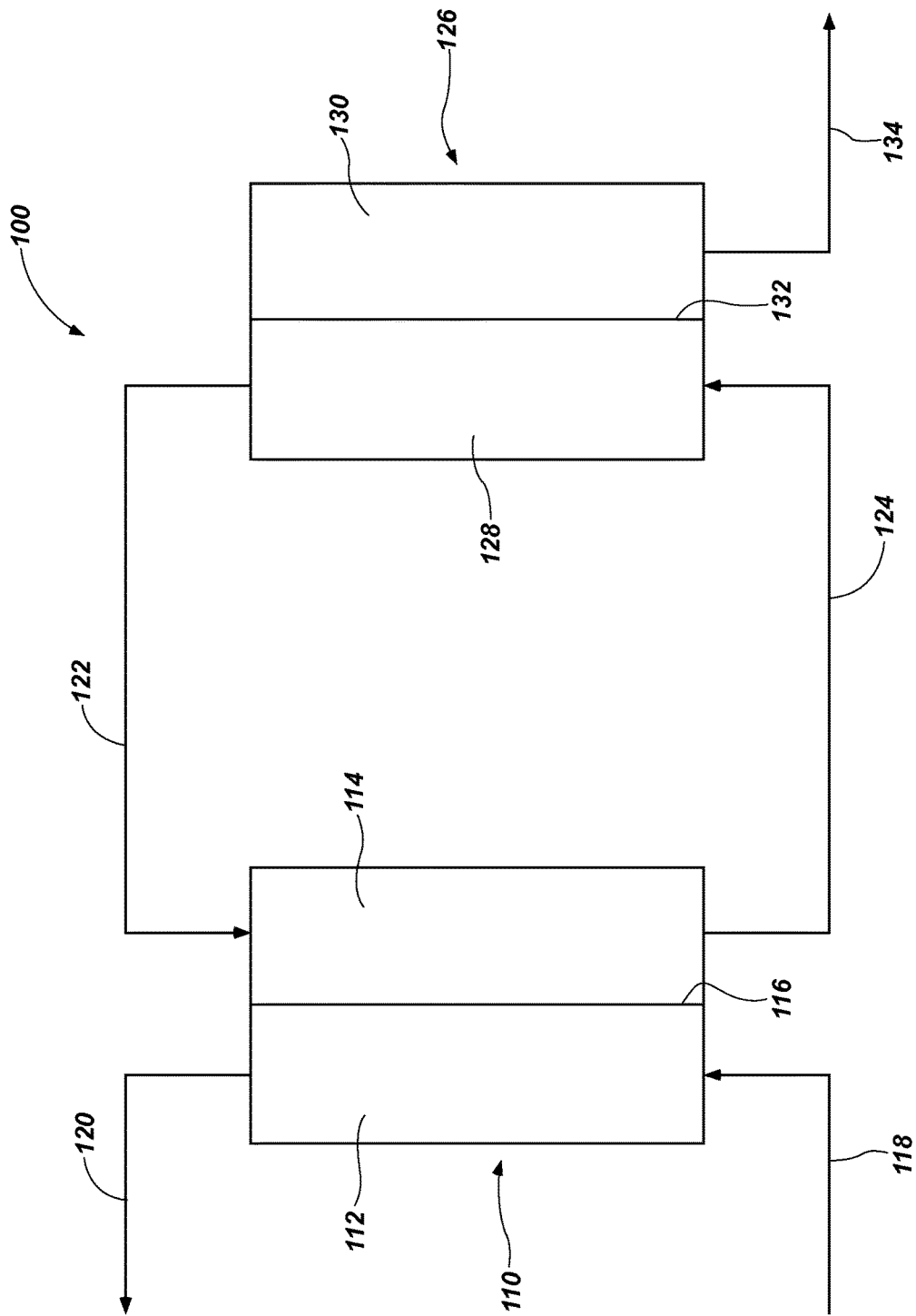
FIG. 1 is a schematic drawing of an aqueous liquid treatment system, in accordance with an embodiment of the present disclosure.

A phosphazene compound for use as a draw solute and a triazine compound for use as a draw solute are disclosed, as are methods of forming the phosphazene compound and the triazine compound, and methods of using at least one of the phosphazene compound and the triazine compound to treat an aqueous liquid. The phosphazene compound may include a plurality of salt-terminated pendant groups bonded to phosphorus atoms of a plurality of phosphorus-nitrogen units. The triazine compound may include a plurality of salt-terminated pendant groups bonded to carbon atoms of a triazine ring. At least one of the phosphazene compound and the triazine compound may be used as a draw solute in a draw solution to separate or remove water from an aqueous feed liquid by forward osmosis. The draw solution including at least one of the phosphazene compound and the triazine compound may have a greater osmotic pressure than the aqueous feed liquid, facilitating an osmotic pressure gradient through a semi-permeable membrane to draw the water into the draw solution while leaving at least one solute in the aqueous feed liquid. The at least one solute may a contaminant (e.g., organic or inorganic impurity) in the aqueous feed liquid. Each of the phosphazene compound and the triazine compound disclosed herein may enable a more energy efficient and less costly method and system of aqueous liquid treatment as compared to conventional forward osmosis methods and systems utilizing conventional draw solutes.

The following description provides specific details, such as equipment types, material compositions, and processing conditions in order to provide a thorough description of embodiments of the present disclosure. However, a person of ordinary skill in the art will understand that the embodiments of the present disclosure may be practiced without employing these specific details. Indeed, the embodiments of the present disclosure may be practiced in conjunction with conventional systems and methods employed in the industry. In addition, only those process components and acts necessary to understand the embodiments of the present disclosure are described in detail below. A person of ordinary skill in the art will understand that some process components and acts are not described herein but that using various conventional process components and acts would be in accord with the present disclosure. The drawings accompanying the present application are for illustrative purposes only, and are not meant to be actual views of any particular material, device, or system. The drawings are not necessarily drawn to scale.

In one embodiment of the present disclosure, a phosphazene compound for use as a draw solute is described. The phosphazene compound may include a plurality of salt-terminated pendant groups bonded to phosphorus atoms of a plurality of phosphorus-nitrogen units. As used herein, the term "salt-terminated pendant group" means and includes a pendant group having at least one terminal salt functional group. Each phosphorus-nitrogen unit of the phosphazene compound includes a double bond between the phosphorus atom and the nitrogen atom and each phosphorus-nitrogen unit is bonded to an adjacent phosphorus-nitrogen unit through a single bond. The phosphazene compound has the general structure shown below:

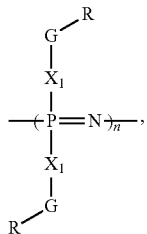

where each $X_1$ is independently an oxygen (O) atom, a sulfur (S) atom, or —NH—; each G and R is as described below; and n is an integer of from 3 to 5. The pendant groups on the phosphazene compound may be electron withdrawing groups to increase dissociation of the phosphazene compound in the draw solution.

Each G group may independently be an aliphatic linkage, a cyclic linkage, —CO—, —SO$_2$—, —SO—, —PO—, —O—, —S—, —NH—, or a combination thereof. As used herein, the term "aliphatic linkage" means and includes a saturated or unsaturated, linear or branched hydrocarbon group, such as an alkylene group, an alkenylene group, and an alkynylene group. A suitable alkylene group may be a saturated linear or branched hydrocarbon group having from 1 to 10 carbon atoms, such as methylene, ethylene, 1,3-propylene, 1,2-buylene, 1,2-butylene, pentylene, hexylene, heptylene, octylene, nonylene, and decalene. A suitable alkenylene group may be an unsaturated linear or branched hydrocarbon group including from 2 to 10 carbon atoms and at least one carbon-carbon double bond. A suitable alkenylene group may be an unsaturated linear or branched hydrocarbon group including from 2 to 10 carbon atoms and at least one carbon-carbon triple bond. Optionally, the aliphatic group may include one or more heteroatom (i.e., an element other than carbon and hydrogen, such as oxygen, nitrogen, sulfur, and silicon). As used herein, the term "cyclic linkage" means and includes at least one closed ring hydrocarbon group, such as an alicyclic group, an arylene group, or a combination thereof. A suitable alicyclic group may be a closed ring hydrocarbon group including from 5 to 8 carbons, such as cyclopentylene, cyclohexylene, cycloheptylene, cyclooctylene, and alkyl-substituted derivatives thereof. A suitable arylene group may include a closed aromatic ring or closed aromatic ring system such as phenylene, biphenylene, napthylene, anthrylene, and alkyl-substituted derivatives thereof. Optionally, the cyclic linkage may include one or more heteroatom. By way of non-limiting example, the cyclic linkage may be a heteroarylene group, such as furylene, thienylene, pyridylene, isoquinolinylene, indolylene, isoindolylene, triazonlylene, pryrrolylene, tetrazolylene, imidazolylene, pyrazolylene, oxazolylene, thiazolylene, benzofuranylene, benzothiophenylene, carbazolylene, benzoxazolylene, pyrimidinylene, benzimidazolylene, quinozalinylene, benzothiazolylene, naphthyridinylene, isoxaolylene, isothiazolylene, purinylene, quinazolinylene, pyrazinylene, pyridazinylene, triazinylene, tetrazinylene, oxadiazolylene, and thiadiazolylene. In at least some embodiments, each G group is phenylene.

Each R may independently be a salt functional group. As used herein, the term "salt functional group" means and includes a neutrally charged functional group formed by combining an anionic functional group and a cationic counterion, or by combining a cationic functional group and an anionic counterion. By way of non-limiting example, if the salt functional group is formed by combining an anionic functional group and an cationic counterion, the salt functional group may be a carboxylate salt group, a sulfonate salt group, or a phosphonate salt group, which have the following structures, respectively:

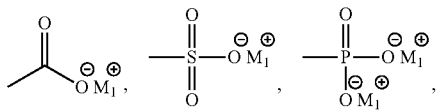

where $M_1$ is independently a mono-valent or multi-valent cationic counterion including, but not limited to, an alkali metal, such as lithium (Li$^+$), sodium (NO, or potassium (K$^+$); ammonium (NH$_4^+$); an alkali earth metal, such as calcium (Ca$^{2+}$), or magnesium (Mg$^{2+}$); a heavy metal, such as zinc (Zn$^{2+}$); a quaternary ammonium (($R_1$)$_4$N$^+$, ($R_1$)$_3$NH$^+$, ($R_1$)$_2$NH$_2^+$, $R_1$NH$_3^+$), where each $R_1$ is independently hydrogen (H), an substituted or unsubstituted alkyl group including from 1 to 8 carbon atoms, or a substituted or unsubstituted aryl group including 5 to 8 carbon atoms; or a quaternary phosphonium, such as ($R_1$)$_4$P$^+$, ($R_1$)$_3$PH$^+$, ($R_1$)$_2$PH$_2^+$, or $R_1$PH$_3^+$, where $R_1$ is defined as previously described. In at least some embodiments, each R is a carboxylate salt group including a sodium counterion.

By way of additional non-limiting example, if the salt functional group is formed by combining a cationic functional group and an anionic counterion, the salt functional group may be a quaternary ammonium salt, or a quaternary phosphorus salt, which have the following structures, respectively:

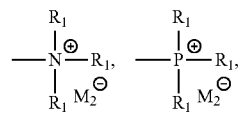

where $R_1$ is defined as previously described; and $M_2$ is a mono-valent anionic counterion or a multi-valent anionic counterion including, but not limited to, a halide, such as fluorine (F$^-$), chlorine (Cl$^-$), bromine (Br), or iodine (F); hydroxide; nitrate; a sulfate, such as sulfate (SO$_4^{2-}$), monopotassium sulfate (KSO$_4^-$), monosodium sulfate (NaSO$_4^-$), and hydrogen sulfate (HSO$_4^-$); a carboxylate, such as formate, acetate, propionate, trifluoroacetate, succinate, salicylate, DL-aspartate, D-aspartate, L-aspartate, DL-glutamate, D-glutamate, L-glutamate, glycerate, succinate, DL-tartarate, D-tartarate, L-tartarate, (R)-(−)-mandelate, (S)-(+)- mandelate, citrate, mucate, maleate, malonate, benzoate, DL-malate, D-malate, L-malate, hemi-malate, 1-adamantaneacetate, 1-adamantanecarboxylate, flavianate, sulfonoacetate, (±)-lactate, L-(+)lactate, D-(−)-lactate, pamoate, D-alpha-galacturonate, glycerate, DL-ascorbate, D-ascorbate, L-ascorbate, DL-cystate, D-cystate, L-cystate, DL-homocystate, D-homocystate, L-homocystate, DL-cysteate, D-cysteate, L-cysteate, (4S)hydroxy-L-proline, cyclopropane-1,1-dicarboxylate, 2,2dimethylmalonate, squarate, tyrosine anion, proline anion, fumarate, 1-hydroxy-2-naphthoate, phosphonoacetate, carbonate, bicarbonate, 3-phosphonopropionate, DL-pyroglutamate, D-pyroglutamate, or L-pyroglutamate; a sulfonate, such as methanesulfonate, toluenesulfonate, benzenesulfonate, trifluoromethylsulfonate, ethanesulfonate, (±)-camphorsulfonate, naphthalenesulfonate, 1R-(−)-camphorsulfonate, 1S-(+)-camphorsulfonate, 2-mesitylenesulfonate, 1,5-naphthalenedisulfonate, 1,2-ethanedisulfonate, 1,3-propanedisulfonate, 3-(N-morpholino)propane sulfonate, biphenylsulfonate, isethionate, or 1-hydroxy-2-naphthalenesulfonate); a sulfamate; a phosphate, such as phosphate ($PO_4^{3-}$), dihydrogen phosphate ($H_2PO_4^-$), potassium hydrogen phosphate ($KHPO_4^-$), dipotassium phosphate ($K_2PO_4^-$), potassium phosphate ($KPO_4^{2-}$), sodium hydrogen phosphate ($NaHPO_4^-$), disodium phosphate ($Na_2PO_4^-$), sodium phosphate ($NaPO_4^{2-}$), calcium phosphate, calcium dihydrogen phosphate, calcium hydrogen phosphate, calcium phosphate tribasic, or hexafluorophosphate; and a phosphonate, such as 2-carboxyethylphosphonate, or phenylphosphonate.

The phosphazene compound may be cyclic, branched, or linear. In at least some embodiments, the phosphazene compound is cyclic and includes three phosphorus-nitrogen units (n=3). A general structure for the phosphazene compound where n=3 is shown below:

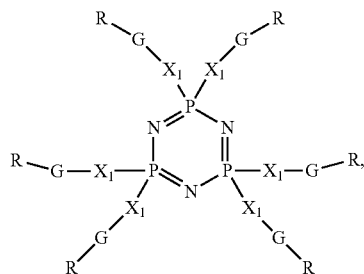

where $X_1$, G, and R are defined as previously described. While various embodiments herein describe or illustrate the phosphazene compound as a six-membered cyclic compound, i.e., n=3, the phosphazene compound may be from a six-membered to an eight-membered cyclic compound.

The $X_1$, G, and R groups of the phosphazene compound may be selected such that the phosphazene compound is of sufficient viscosity to function as the draw solute in the draw solution. The viscosity of the phosphazene compound may be less than or equal to about 200 centipoise (cp). Since the viscosity of the phosphazene compound is related to its molecular weight, the $X_1$, G, and R groups may be selected such that the molecular weight of the phosphazene compound is less than or equal to about 1500.

In at least some embodiments, the phosphazene compound has one of the structures shown below:

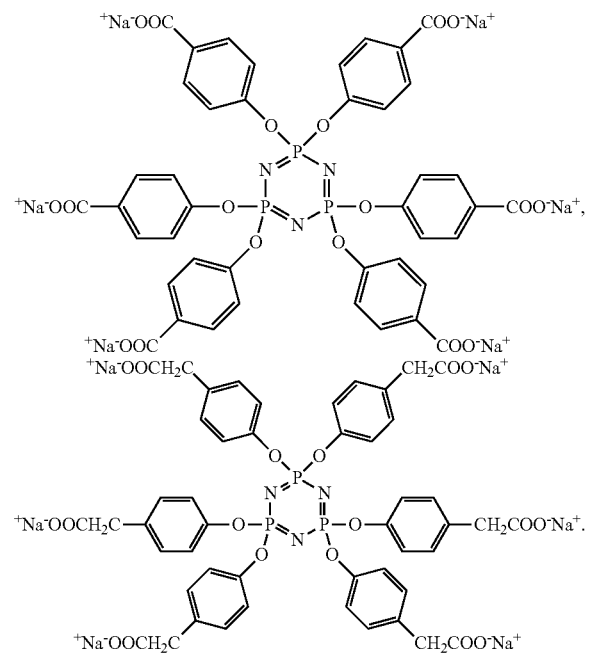

While the illustrated phosphazene compounds include six of the same salt-terminated pendant groups, G groups, and $X_1$ groups, phosphazene compounds having different combinations of salt-terminated pendant groups, G groups, and $X_1$ groups as described above, may be produced, depending on the desired properties of the phosphazene compound. Thus, the phosphazene compound may be symmetrical or asymmetrical.

A non-limiting reaction scheme for the preparation of a phosphazene compound from a halogenated phosphazene compound is shown below:

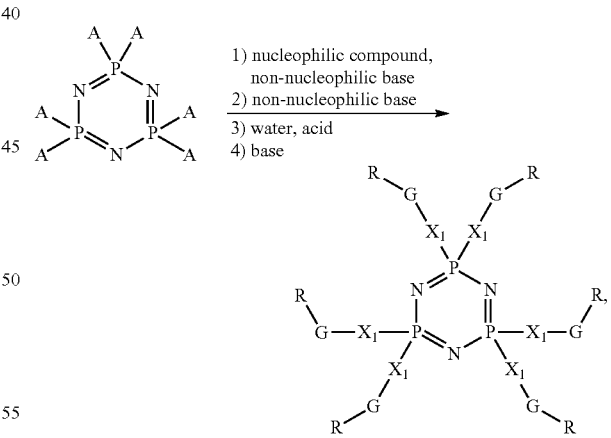

where $X_1$, G, and R are defined as previously described; and each A is independently a halogen, such as F⁻, or Cl⁻. The reaction scheme is described in detail below.

A nucleophilic compound and a first non-nucleophilic base may be added or introduced to the halogenated phosphazene compound to facilitate at least one nucleophilic substitution reaction and form an at least partially substituted phosphazene compound including at least one pendant group having a salt functional group precursor. As used herein, the term "nucleophilic compound" means and includes an organic compound having a free electron pair (e.g., a N, O, S, or P atom, or a C atom that may donate its electron pair) and including a salt functional group precursor, such as a carboxylate-containing compound, a sulfonate-containing compound, or a phosphonate-containing compound. In at least some embodiments, the nucleophilic compound is a carboxylate-containing compound. As used herein, the term "non-nucleophilic base" means and includes a base that is slow to act as a nucleophile in a substitution reaction. Non-limiting examples of suitable non-nucleophilic bases include tertiary organic amines, such as diisopropylethylamine (DIPEA); Group I metal cation hydrides, such as sodium hydride (NaH); Group II metal cation hydrides; Group I metal cation dialkylamides, such as lithium diisopropylamide ($C_6H_{14}LiN$); Group I metal cation bis(trialkylsilyl)amides, such as potassium bis(trimethylsilyl)amide ($C_6H_{18}KNSi_2$), and sodium bis(trimethylsilyl)amide ($C_6H_{18}NaNSi_2$); Group II metal cation bis(trialkylsilyl) amides; Group I metal cation tertiary-alkoxides, such as sodium tert-butoxide ($C_4H_9NaO$), and potassium tert-butoxide ($C_4H_9KO$); and Group II metal cation tertiary alkoxides. In at least some embodiments, the first non-nucleophilic base is NaH. As used herein, the term "halogenated phosphazene compound" means and includes a linear, branched, or cyclic phosphazene compound having at least one halogen atom bonded to a phosphorus atom thereof. By way of non-limiting example, the halogenated phosphazene compound may be a cyclic phosphazene compound including from 3 to 5 phosphorus-nitrogen units and at least one halogen bound to each phosphate atom thereof. In at least some embodiments, the halogenated phosphazene compound is hexachlorotriphosphazene ($N_3P_3Cl_6$), which is commercially available from numerous sources, such as from Sigma-Aldrich Co. (St. Louis, Mo.). While specific embodiments herein describe using $N_3P_3Cl_6$ as the halogenated phosphazene compound to form a specific draw solute, additional halogenated phosphazene compounds, such as octachlorocyclotetraphosphazene ($N_4P_4Cl_8$), may be used, depending on desired characteristics of the draw solute to be formed (e.g., to form a draw solute including additional salt functional groups).

The nucleophilic substitution reaction may be conducted in at least one aprotic solvent in which the halogenated phosphazene compound is at least partially soluble. The at least one aprotic solvent may include, but is not limited to, a $C_5$-$C_8$ hydrocarbon (i.e., of straight-chain, branched, or cyclic configuration), such as a pentane, a hexane, a cyclohexane, an iso-octane, an ether (e.g., diethyl ether, tetrahydrofuran, 1,4-dioxane, glycol ethers including 1,2-dimethoxyethane), or combinations thereof. In at least some embodiments, the aprotic solvent is a combination of tetrahydrofuran (THF) and 1,4-dioxane. By way of non-limiting example, a first solution including the nucleophilic compound and a first aprotic solvent (e.g., 1,4-dioxane) may be added or introduced to a second solution including the first non-nucleophilic base and a first aprotic solvent (e.g., THF) to form a third solution. A fourth solution including the halogenated phosphazene compound and a third aprotic solvent (e.g., 1,4-dioxane) may be added or introduced to the third solution to form a reaction mixture enabling the formation of the at least partially substituted phosphazene compound.

At least one molar equivalent of the nucleophilic compound may be used relative to the halogenated phosphazene compound to form the at least partially substituted phosphazene compound (e.g., a fully-substituted phosphazene compound, or a less-than-fully-substituted phosphazene compound). To form a fully-substituted phosphazene compound, the nucleophilic compound may be added or introduced in molar excess relative to the halogenated phosphazene compound. By way of non-limiting example, if the halogenated phosphazene compound includes six halogen atoms, at least six molar equivalents of the nucleophilic compound may be used relative to the halogenated phosphazene compound to form a fully-substituted phosphazene compound. As used herein, the term "fully-substituted phosphazene compound" means and includes a phosphazene compound in which each phosphorus atom of the phosphazene compound has two pendant groups, which are provided by reaction between the halogenated phosphazene compound and the nucleophilic compound. A non-limiting example of a nucleophilic substitution reaction enabling the formation of a fully-substituted phosphazene compound is shown below, where the halogenated phosphazene compound is $N_3P_3Cl_6$, and the nucleophilic compound is a carboxylic acid ester:

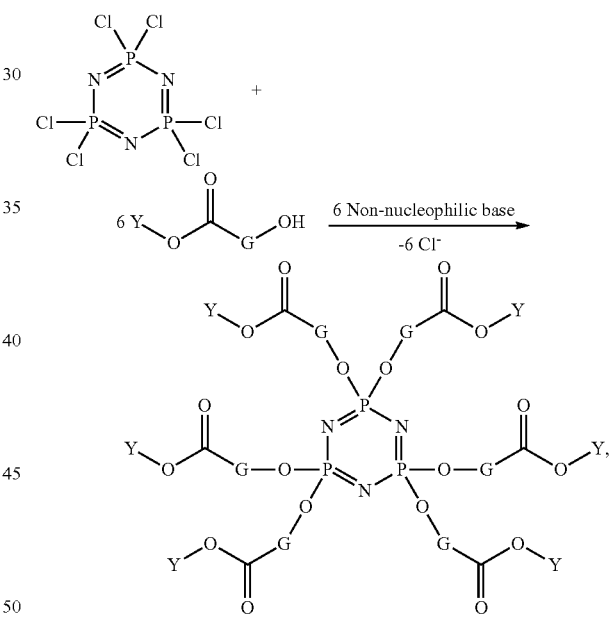

where G is defined as previously described; and each Y is independently an aliphatic group or a cyclic group, such as a methyl, ethyl, propyl, or butyl group. While the fully-substituted phosphazene compound is the predominant reaction product formed when six molar equivalents of carboxylic acid ester (e.g., 4-ethylcarboxylatophenol), and six molar equivalents of non-nucleophilic base (e.g., NaH) are reacted with the $N_3P_3Cl_6$ in a suitable aprotic solvent (e.g., THF, 1,4-dioxane), other partially-substituted reaction products may also be formed. The fully-substituted phosphazene compound may account for at least about 30% of the total nucleophilic substitution reaction products, with the remainder of the nucleophilic substitution reaction products including phosphazene compounds substituted with a statistical mixture of chlorine atoms, and carboxylic acid ester groups based on a molar ratio of the reagents used.

The fully-substituted phosphazene compound may, alternatively, be formed using multiple nucleophilic substitution reactions. By way of non-limiting example, if the halogenated phosphazene compound includes six halogen atoms, less than six molar equivalents of the nucleophilic compound may be used relative to the halogenated phosphazene compound to form a less-than-fully-substituted phosphazene compound (i.e., partially-substituted phosphazene compound). As used herein, the term "less-than-fully-substituted phosphazene compound" means and includes a phosphazene compound including from one halogen atom to $2w\text{-}1$ halogen atoms bonded to the phosphorus atoms, where w is the number of phosphorus atoms in the phosphazene compound (excluding pendant phosphorus atoms). By way of non-limiting example, a phosphazene compound including three phosphorus atoms, $w=3$, is a less-than-fully-substituted phosphazene compound if it includes between one halogen atom and five halogen atoms. The less-than-fully-substituted phosphazene compound may be subjected to at least one subsequent nucleophilic substitution reaction to form the fully-substituted phosphazene compound. The multiple nucleophilic substitution reactions may occur as a one-pot process or a stepwise process. As used herein, the term "one-pot process" means and includes a synthesis process utilizing two or more chemical reactions, wherein a reaction product of a sequentially earlier chemical reaction is used for a subsequent chemical reaction without isolation and/or purification. As used herein, the term "stepwise process" means and includes a synthesis process utilizing two or more chemical reactions, wherein a reaction product of a sequentially earlier chemical reaction is isolated and/or purified prior to use in a subsequent chemical reaction. If the fully-substituted phosphazene compound is formed using multiple nucleophilic substitution reactions, the same or different nucleophilic compounds may be utilized in each nucleophilic substitution reaction. Thus, the fully-substituted phosphazene compound may have the same or different pendant groups.

A non-limiting example of using multiple nucleophilic substitution reactions to form a fully-substituted phosphazene compound is shown below, where the halogenated phosphazene compound is $N_3P_3Cl_6$, and the nucleophilic compound in each nucleophilic substitution reactions is a carboxylic acid ester:

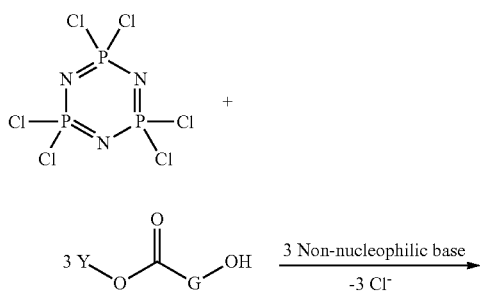

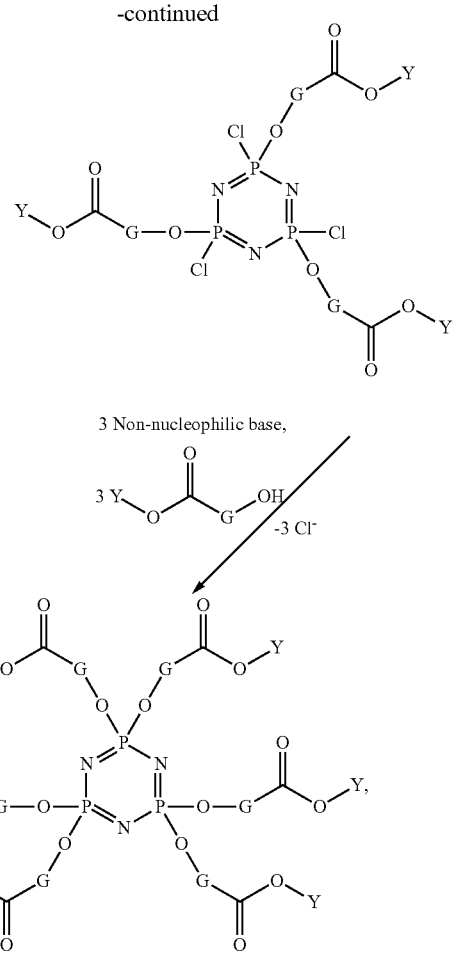

where G and Y are defined as previously described. While the less-than-fully-substituted phosphazene compound is the predominant reaction product formed when three molar equivalents of carboxylic acid ester (e.g., 4-ethylcarboxylatophenol), and three molar equivalents of non-nucleophilic base (e.g., NaH) are reacted with the $N_3P_3Cl_6$ in a suitable aprotic solvent (e.g., THF, 1,4-dioxane), other reaction products may also be formed. Likewise, while the fully-substituted phosphazene compound is the predominant reaction product formed when three molar equivalents of carboxylic acid ester (e.g., 4-ethylcarboxylatophenol), and three molar equivalents of non-nucleophilic base (e.g., NaH) are reacted with the less-than-fully-substituted phosphazene compound in a suitable aprotic solvent (e.g., THF, 1,4-dioxane), other reaction products may also be formed.

The at least one nucleophilic substitution reaction may be conducted under anhydrous conditions, at atmospheric pressure or greater, and at a temperature with a range of from about 0° C. to about 130° C., such as from about 50° C. to about 100° C., or from about 80° C. to about 90° C. The reaction mixture may be agitated (e.g., via stirring, ultrasonically agitating, shaking a containment vessel) for a sufficient amount of time to facilitate partial or full completion of the nucleophilic substitution reaction.

The at least partially substituted phosphazene compound (e.g., the fully-substituted phosphazene compound, or the less-than-fully-substituted phosphazene compound) may be isolated. By way of non-limiting example, the reaction mixture may be filtered and subjected to rotary evaporation to yield a crude material including the at least partially substituted phosphazene compound. The crude material may be dissolved in a suitable aprotic solvent, such as a combination of diethyl ether and THF, to form a substituted phosphazene mixture. The substituted phosphazene mixture may be added or introduced to an additional solvent, such as hexane, to precipitate the at least partially substituted phosphazene compound. The at least partially substituted phosphazene compound may be separated by conventional techniques (e.g., by filtration) and dried. If the at least partially substituted phosphazene compound is less-than-fully-substituted, it may be subjected to one or more additional nucleophilic substitution reactions (e.g., to form the fully-substituted phosphazene compound) in a stepwise process, as described above. The at least partially substituted phosphazene compound may be hydrolyzed as described in detail below.

The at least partially substituted phosphazene compound (e.g., the fully-substituted phosphazene compound, or the less-than-fully-substituted phosphazene compound) may be hydrolyzed to form an acidic phosphazene compound including at least one acid-terminated pendant group. As used herein, the term "acid-terminated pendant group" means and includes a pendant group including at least one terminal acid group, such as a carboxylic acid group, a sulfonic acid group, or a phosphonic acid group. A phosphazene solution including the at least partially substituted phosphazene compound may be added or introduced to a base solution including a second non-nucleophilic base. The second non-nucleophilic base may be the same as or different than the first non-nucleophilic base described above. In at least some embodiments, the second non-nucleophilic base is $C_4H_9KO$. The resulting mixture may be agitated and added or introduced to water to form a reaction mixture. The pH of the reaction mixture may be adjusted with acid (e.g., hydrochloric acid) until the phosphazene compound including at least one acid-terminated pendant group precipitates from the reaction mixture. The acidic phosphazene compound may be isolated by conventional techniques, such as at least one of filtration, centrifugation, and evaporation. By way of non-limiting example, if the at least partially substituted phosphazene compound is a fully-substituted cyclotriphosphazene compound including carboxylic acid ester-terminated pendant groups, the second non-nucleophilic base (e.g., $C_4H_9KO$) may be added or introduced to the fully-substituted cyclotriphosphazene compound, followed by exposure to water in the presence of an acid catalyst to form an acidic cyclotriphosphazene compound including carboxylic acid-terminated pendant groups according to the hydrolysis reaction below:

-continued

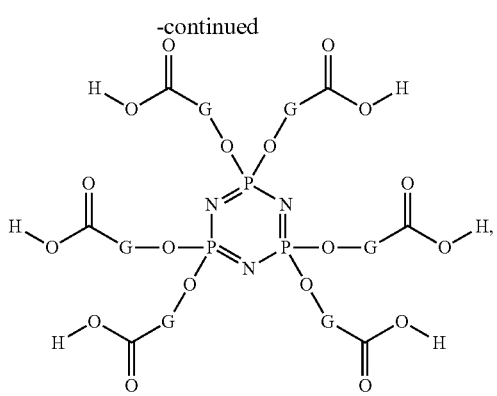

where G and Y are defined as previously described.

The acidic phosphazene compound including the at least one acid-terminated pendant group may undergo a neutralization reaction with a base to form the phosphazene compound including at least one salt-terminated pendant group, which may be used as the draw solute. The base may be a conventional base having an appropriate cation of the desired salt-terminated pendant group. By way of non-limiting example, the base may be a $Li^+$, $Na^+$, $K^+$, $NH_4^+$, $Ca^{2+}$, $Mg^{2+}$, $Zn^{2+}$, or $(R_1)_4N^+$ (where $R_1$ is defined as previously described) containing base. In at least some embodiments, the base is sodium hydroxide (NaOH). To facilitate the neutralization reaction, an aqueous liquid of the base may be added or introduced to an aqueous suspension of the acidic phosphazene compound. Following the neutralization reaction, the phosphazene compound may be isolated by conventional techniques, such as at least one of evaporation, filtration, and centrifugation. As a non-limiting example, if the acidic phosphazene compound is a cyclotriphosphazene compound including carboxylic acid-terminated pendant groups, the base (e.g., NaOH) may be added or introduced to the cyclotriphosphazene compound to form a final cyclotriphosphazene compound including carboxylic acid salt-terminated pendant groups according to the neutralization reaction below:

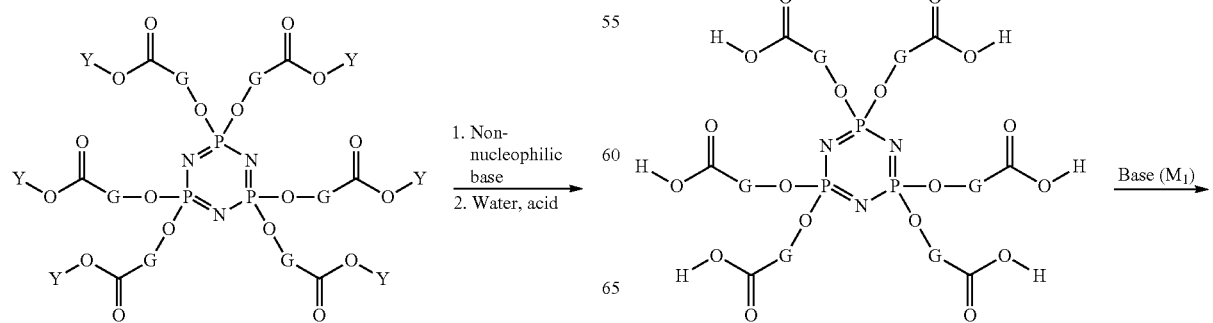

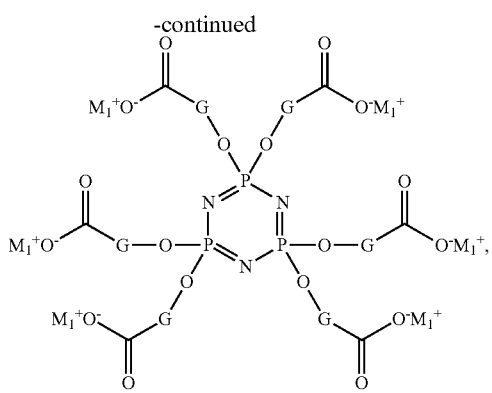

where $M_1$ and G are defined as previously described.

The detailed reaction scheme below illustrates a non-limiting example of a conversion of $N_3P_3Cl_6$ to sodium hexa(4-carboxylatophenoxy)cyclotriphosphazene salt, which may be used as the draw solute:

$N_3P_3Cl_6$ in 1,4-dioxane may be reacted with 4-ethylcarboxylatophenol and NaH in THF to form a reaction solution including hexa(4-ethylcarboxylatophenoxy)cyclotriphosphazene. The hexa(4-ethylcarboxylatophenoxy)cyclotriphosphazene may be isolated and dissolved in THF. $C_4H_9KO$ in THF may be added or introduced to the hexa(4-ethylcarboxylatophenoxy)cyclotriphosphazene in THF. The resulting mixture may be added or introduced to water to hydrolyze the hexa(4-ethylcarboxylatophenoxy) cyclotriphosphazene and form hexa(4-carboxyphenoxy) cyclotriphosphazene. The hexa(4-carboxyphenoxy) cyclotriphosphazene may be isolated and suspended in water. Aqueous NaOH may be added or introduced to the hexa(4-carboxyphenoxy)cyclotriphosphazene in aqueous suspension to neutralize carboxylic acid groups of the hexa (4-carboxyphenoxy)cyclotriphosphazene and form the sodium hexa(4-carboxylatophenoxy)cyclotriphosphazene salt. The sodium hexa(4-carboxylatophenoxy)cyclotriphosphazene salt may be isolated and used as the draw solute.

In another embodiment of the present disclosure, a triazine compound for use as a draw solute is described. The

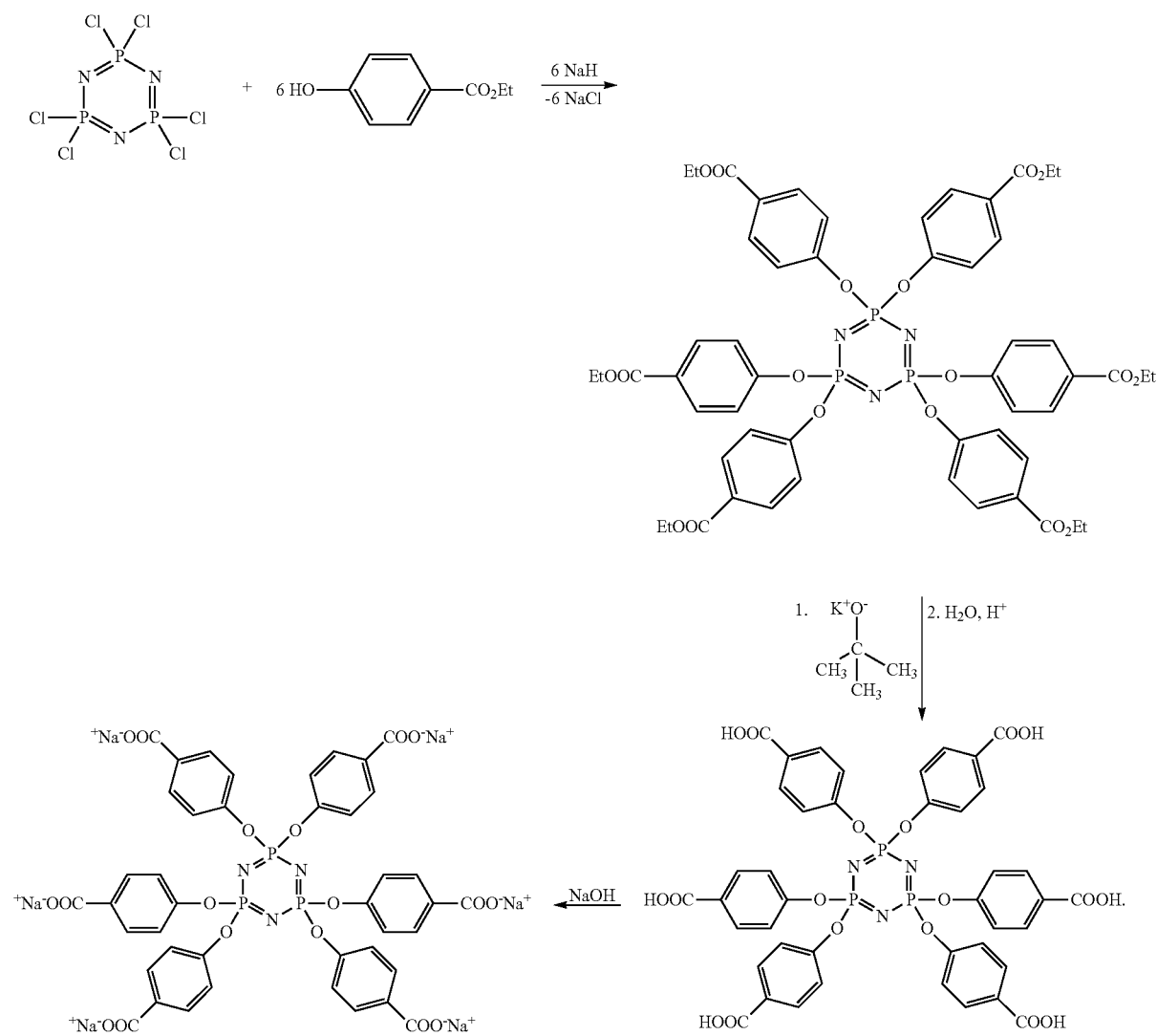

triazine compound includes a plurality of salt-terminated pendant groups bonded to carbon atoms of a triazine ring. The triazine ring may be a 1,3,5-triazine ring, a 1,2,4-triazine ring, or a 1,2,3-triazine ring. In at least some embodiments, the triazine ring is a 1,3,5-triazine ring and the triazine compound has the general structure shown below:

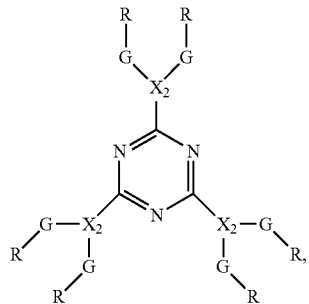

where G, R, and n are defined as previously described; and $X_2$ is an nitrogen (N) atom, a phosphorus (P) atom, —CH—, or —SiH—. The pendant groups on the triazine compound may be electron withdrawing groups to increase dissociation of the triazine compound in the draw solution. While various embodiments herein describe or illustrate the triazine compound as including a 1,3,5-triazine ring, the triazine compound may, alternatively, include a 1,2,3-triazine ring or a 1,2,4-triazine ring, depending on the desired properties of the triazine compound.

The $X_2$, G, and R groups of the triazine compound may be selected such that the triazine compound is of sufficient viscosity to function as the draw solute in the draw solution. The viscosity of the triazine compound may be less than or equal to about 200 cp. Since the viscosity of the triazine compound is related to its molecular weight, the $X_1$, G, and R groups may be selected such that the molecular weight of the triazine compound is less than or equal to about 1500.

In at least one embodiment, the triazine compound has the structure shown below:

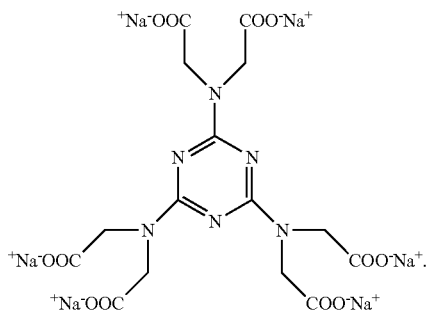

While the illustrated triazine compound includes three of the same salt-terminated pendant groups, triazine compounds having different salt-terminated pendant groups, as described above, may be produced, depending on the desired properties of the triazine compound.

A non-limiting reaction scheme for the preparation of a triazine compound from a halogenated triazine compound is show below:

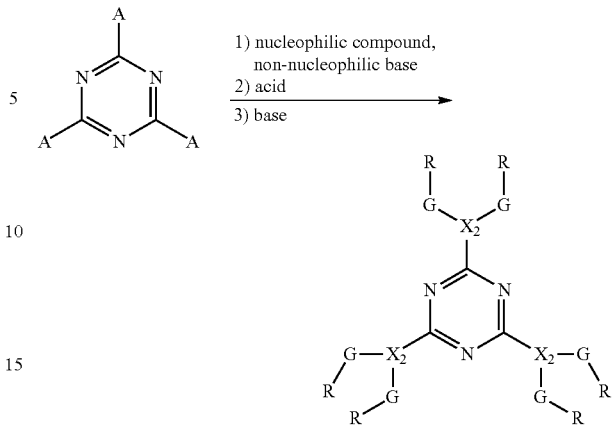

where A, $X_2$, G, and R are defined as previously described. The reaction scheme is described in detail below.

A nucleophilic compound and a non-nucleophilic base may be added or introduced to the halogenated triazine compound to facilitate at least one nucleophilic substitution reaction and form an at least partially substituted triazine compound (e.g., a fully-substituted triazine compound, or a less-than-fully-substituted triazine compound) including at least one pendant group having a salt functional group precursor. The nucleophilic compound may be any known organic compound having a free electron pair and including a salt functional group precursor, such as a carboxylate-containing compound, a sulfonate-containing compound, or a phosphonate-containing compound. In at least some embodiments, the nucleophilic compound is a carboxylate-containing compound. The non-nucleophilic base may be any known base that is slow to act as a nucleophile in a substitution reaction. By way of non-limiting example, the non-nucleophilic base may include at least one of sodium hydride (NaH), sodium tert-butoxide ($C_4H_9NaO$), potassium tert-butoxide ($C_4H_9KO$), lithium diisopropylamide ($C_6H_{14}LiN$), potassium bis(trimethylsilyl)amide ($C_6H_{18}KNSi_2$), sodium bis(trimethylsilyl)amide ($C_6H_{18}NaNSi_2$), and diisopropylethylamine (DIPEA). In at least some embodiments, the non-nucleophilic base is DIPEA. The halogenated triazine compound may be any triazine compound including at least one halogen (e.g., F⁻, Cl⁻, Br⁻, I⁻) bound to each carbon atom thereof. In at least some embodiments, the halogenated triazine compound is 2,4,6-trichloro-1,3,5-triazine ($C_3Cl_3N_3$), which is commercially available from numerous sources, such as from Sigma-Aldrich Co. (St. Louis, Mo.). While specific embodiments herein describe using $C_3Cl_3N_3$ as the halogenated triazine compound to form a specific draw solute, additional halogenated triazine compounds may be used, depending on desired characteristics of the draw solute to be formed.

At least one molar equivalent of the nucleophilic compound may be used relative to the halogenated triazine compound to form the at least partially substituted triazine compound. The nucleophilic compound may be added or introduced in molar excess relative to the halogenated triazine compound. By way of non-limiting example, if the halogenated triazine compound includes three halogen atoms, at least three molar equivalents of the nucleophilic compound may be used relative to the halogenated triazine compound to form a fully-substituted triazine compound. As used herein, the term "fully-substituted triazine compound" means and includes a triazine compound in which each carbon atom of the triazine compound has a pendant group bonded thereto, which is provided by the nucleophilic compound. A non-limiting example of a nucleophilic substitution reaction enabling the formation of a fully-substituted triazine compound is shown below, where the halogenated triazine compound is $C_3Cl_3N_3$, and the nucleophilic compound is a carboxylic acid ester:

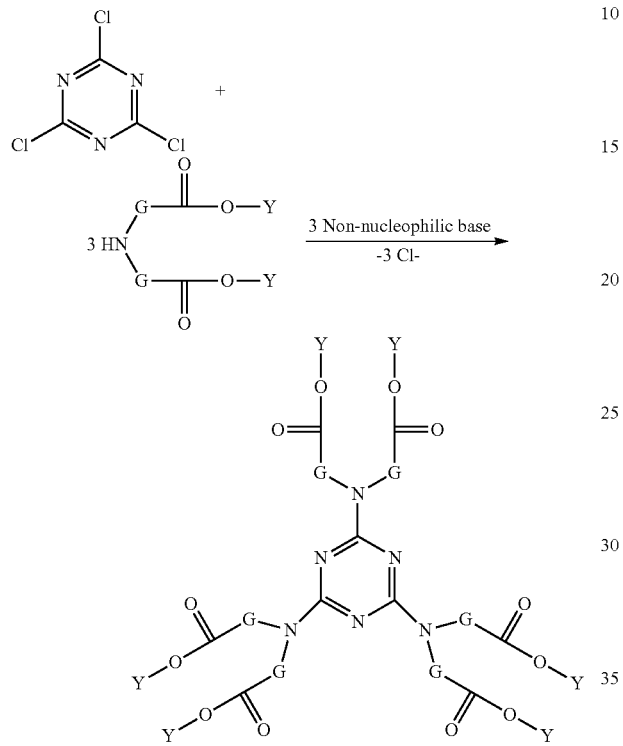

where G and Y are defined as previously described. While the fully-substituted triazine compound is the predominant reaction product formed when three molar equivalents of carboxylic acid ester (e.g., diethyliminodiacetate) and three molar equivalents of non-nucleophilic base (e.g., DIPEA) are reacted with the $C_3Cl_3N_3$ in a suitable aprotic solvent (e.g., THF), other reaction products may also be formed. The fully-substituted triazine compound may account for at least about 30% of the total nucleophilic substitution reaction products, with the remainder of the nucleophilic substitution reaction products including triazine compounds substituted with a statistical mixture of chlorine atoms, and carboxylic acid ester groups based on a molar ratio of the reagents used.

The fully-substituted triazine compound may, alternatively, be formed using multiple nucleophilic substitution reactions. By way of non-limiting example, if the halogenated triazine compound includes three halogen atoms, less than three molar equivalents of the nucleophilic compound may be used relative to the halogenated triazine compound to form a less-than-fully-substituted triazine compound. As used herein, the term "less-than-fully-substituted triazine compound" means and includes a triazine compound including at least one halogen atom to bonded to the carbon atoms of the triazine ring of the triazine compound. The less-than-fully-substituted triazine compound may be subjected to at least one subsequent nucleophilic substitution reaction to form the fully-substituted triazine compound. The multiple nucleophilic substitution reactions may occur as a one-pot process or a stepwise process. If the fully-substituted triazine compound is formed using multiple nucleophilic substitution reactions, the same or different nucleophilic compounds may be utilized in each nucleophilic substitution reaction. Thus, the fully-substituted triazine compound may have the same or different pendant groups.

A non-limiting example of using multiple nucleophilic substitution reactions to form a fully-substituted triazine compound is shown below, where the halogenated triazine compound is $C_3Cl_3N_3$, and the nucleophilic compound in each nucleophilic substitution reactions is a carboxylic acid ester:

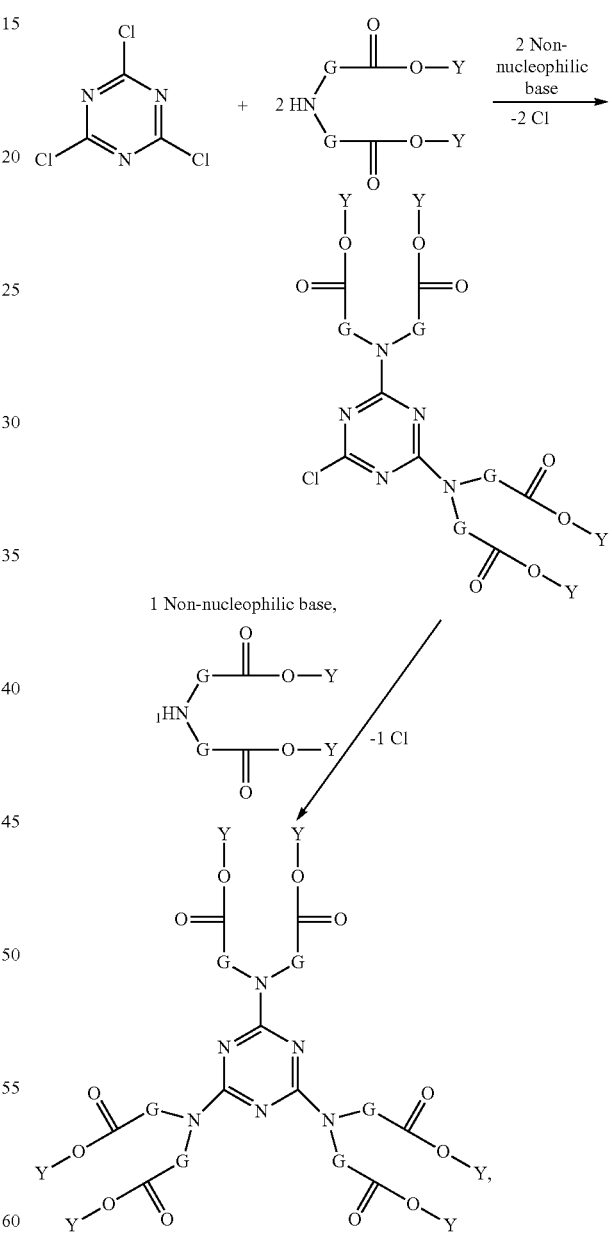

where G and Y are defined as previously described. While the less-than-fully-substituted triazine compound is the predominant reaction product formed when two molar equivalents of carboxylic acid ester (e.g., diethyliminodiacetate), and two molar equivalents of non-nucleophilic base (e.g., DIPEA) are reacted with the $C_3Cl_3N_3$ in a suitable aprotic solvent (e.g., THF), other reaction products may also be formed. Likewise, while the fully-substituted triazine compound is the predominant reaction product formed when at least one molar equivalent of carboxylic acid ester (e.g., diethyliminodiacetate) and at least one molar equivalent of non-nucleophilic base (e.g., DIPEA) are reacted with the less-than-fully-substituted phosphazene compound in a suitable aprotic solvent (e.g., THF), other reaction products may also be formed.

The at least one nucleophilic substitution reaction may be conducted under anhydrous conditions, at atmospheric pressure or greater, and at a temperature with a range of from about 0° C. to about 130° C., such as about 0° C. to about 25° C. The reaction mixture may be agitated (e.g., via stirring, ultrasonically agitating, shaking a containment vessel) for a sufficient amount of time to facilitate a completion of the nucleophilic substitution reaction.

The at least partially substituted triazine compound (e.g., the fully-substituted triazine compound, or the less-than-fully-substituted triazine compound) may be isolated. By way of non-limiting example, the reaction mixture may be filtered and subjected to rotary evaporation to yield a crude material including the at least partially substituted triazine compound. The crude material may be dissolved in a suitable aprotic solvent, such as dichloromethane ($CH_2Cl_2$), to form a substituted triazine mixture. The substituted triazine mixture may be subjected to an aqueous acid wash (e.g., 2% aqueous HCl). The substituted triazine solution may be separated from the aqueous acid wash by conventional techniques and dried using a suitable drying agent, such as anhydrous magnesium sulfate ($MgSO_4$). The organic solvent may then be removed or extracted to yield the at least partially substituted triazine compound. If the at least partially substituted triazine compound is less-than-fully-substituted, the at least partially substituted triazine compound may be subjected to at least one additional nucleophilic substitution reaction (e.g., to form the fully-substituted triazine compound) in a stepwise process, as described above. The at least partially substituted triazine may be hydrolyzed as described in detail below.

The at least partially substituted triazine compound (e.g., the fully-substituted triazine compound, or the less-than-fully-substituted triazine compound) may be hydrolyzed to form an acidic triazine compound including at least one acid-terminated pendant group. A triazine solution including the at least partially substituted triazine compound in at least one solvent (e.g., 1,4-dioxane, water, combinations thereof) may be combined with acid and agitated to form a reaction mixture including the acidic triazine compound. The acidic triazine compound may then be isolated by conventional techniques, such as evaporation. By way of non-limiting example, if the at least partially substituted triazine compound is a fully-substituted triazine compound including carboxylic acid ester-terminated pendant groups, acid (e.g., concentrated HCl) may be combined with a triazine solution including the fully-substituted triazine compound in at least one solvent (e.g., a mixture of 1,4-dioxane and water) to form an acidic triazine compound including carboxylic acid-terminated pendant groups according to the hydrolysis reaction below:

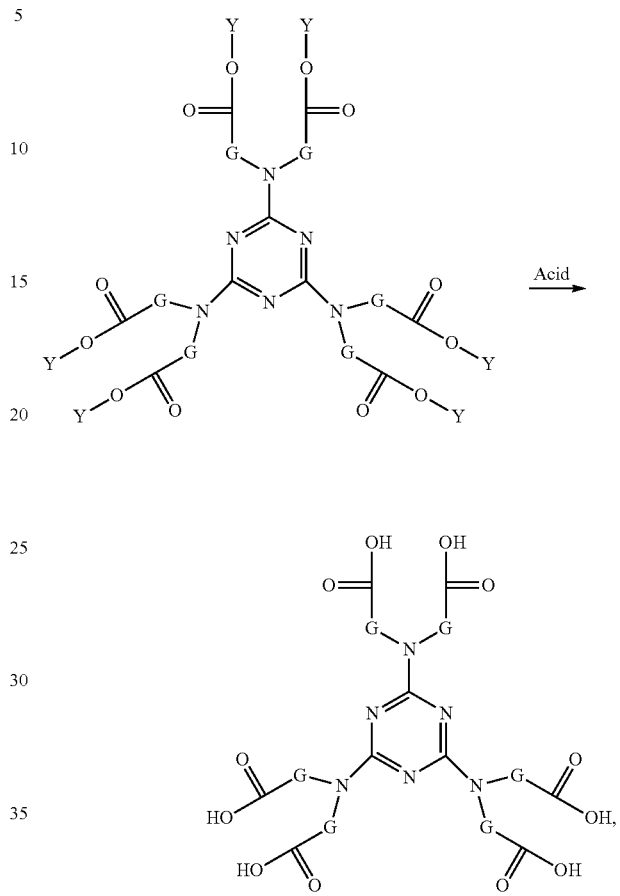

where G and Y are defined as previously described.

The acidic triazine compound including the at least one acid-terminated pendant group may undergo a neutralization reaction with a base to from a triazine compound including at least one salt-terminated pendant group, which may be used as the draw solute. The base may be a conventional base having an appropriate cation of the desired salt-terminated pendant group. By way of non-limiting example, the base may be a $Li^+$, $Na^+$, $K^+$, $NH_4^+$, $Ca^{2+}$, $Mg^{2+}$, $Zn^{2+}$, $(R^1)_4N^+$, or $(R_1)_4N^+$ (where $R_1$ is defined as previously described) containing base. In at least some embodiments, the base is sodium hydroxide (NaOH). To facilitate the neutralization reaction, an aqueous liquid of the base may be added or introduced to an aqueous suspension of the acidic triazine compound. Following the neutralization reaction, the triazine compound may be isolated by conventional techniques, such as evaporation. As a non-limiting example, if the acidic triazine compound includes carboxylic acid-terminated pendant groups, the base (e.g., NaOH) may be added or introduced to the acidic triazine compound to form a triazine compound including carboxylic acid salt-terminated pendant groups according to the neutralization reaction below:

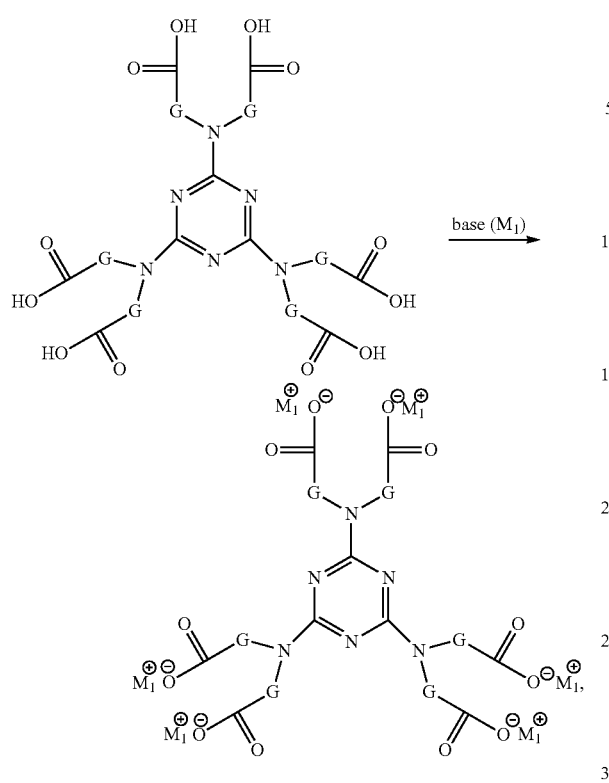

where $M_1$ and G are defined as previously described.

The detailed reaction scheme below illustrates a non-limiting example of a conversion of $C_3Cl_3N_3$ to sodium 2,4,6-tris(iminodiacetic acid)-1,3,5-triazine salt, which may be used as the draw solute:

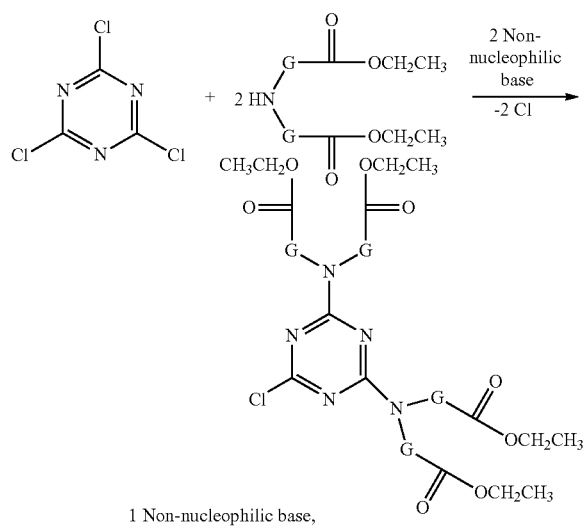

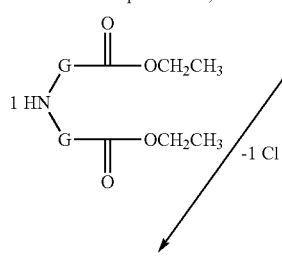

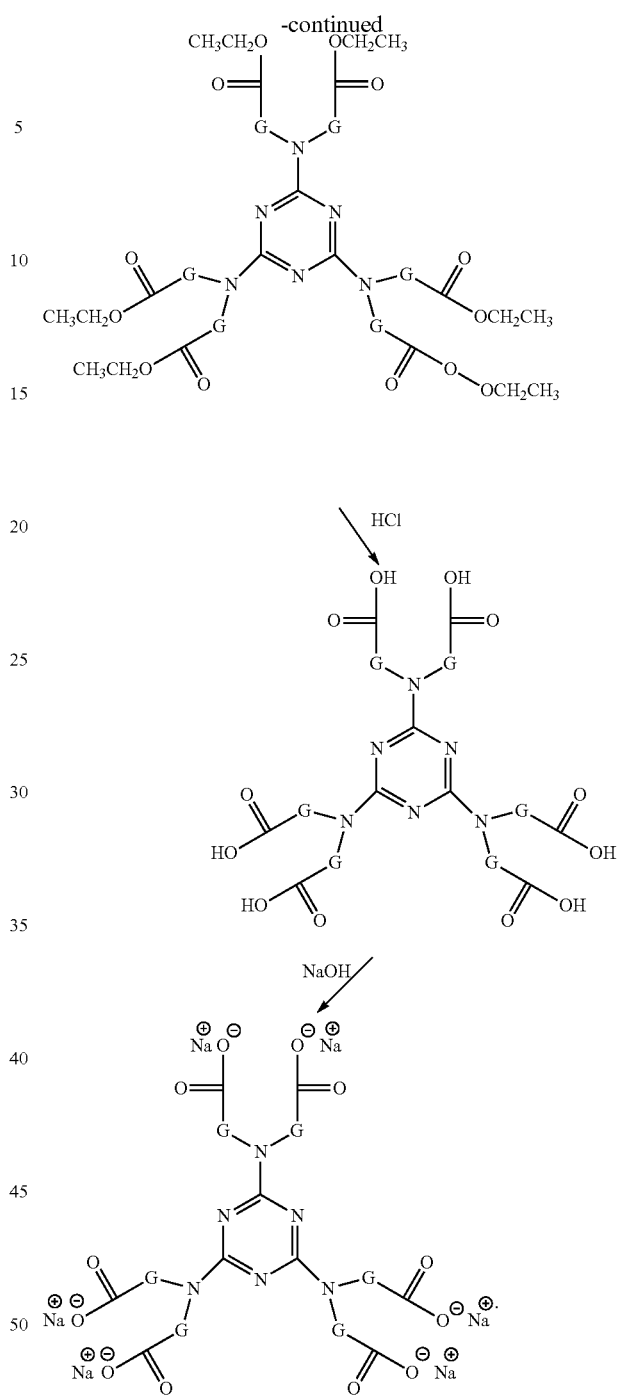

$C_3Cl_3N_3$ and DIPEA in THF may be reacted with excess diethyliminodiacetate to form 2-chloro-4,6-bis(diethyliminodiacetate)-1,3,5-triazine. The 2-chloro-4,6-bis(diethyliminodiacetate)-1,3,5-triazine may be isolated and combined with DIPEA, THF, diethyliminodiacetate, and 1,4-dioxane to form 2,4,6-tris(diethyliminodiacetate)-1,3,5-triazine. The 2,4,6-tris(diethyliminodiacetate)-1,3,5-triazine may be isolated and combined with 1,4-dioxane, water, and HCl to hydrolyze the 2,4,6-tris(diethyliminodiacetate)-1,3,5-triazine and form 2,4,6-tris(iminodiacetic acid)-1,3,5-triazine. The 2,4,6-tris(iminodiacetic acid)-1,3,5-triazine may be isolated and suspended in water. Aqueous NaOH may be added or introduced to the 2,4,6-tris(iminodiacetic acid)-1,3,5- triazine in aqueous suspension to neutralize carboxylic acid groups of the 2,4,6-tris(iminodiacetic acid)-1,3,5-triazine and form the sodium 2,4,6-tris(iminodiacetic acid)-1,3,5-triazine salt. The sodium 2,4,6-tris(iminodiacetic acid)-1,3,5-triazine salt may be isolated and used as desired.

Another embodiment of the present disclosure will now be described with reference to FIG. 1, which schematically illustrates an aqueous liquid treatment system 100. As shown in FIG. 1, the aqueous liquid treatment system 100 includes a forward osmosis device 110 and a filtration device 126. The forward osmosis device 110 receives an aqueous feed liquid 118 in a first chamber 112 and a draw solution 122 in a second chamber 114. The second chamber 114 may be separated from the first chamber 112 by a semi-permeable membrane 116. The aqueous feed liquid 118 may be in contact with a first side of the semi-permeable membrane 116 and the draw solution 122 may be in contact with a second side of the semi-permeable membrane 116.

The aqueous feed liquid 118 may be a solution of water and at least one solute. The at least one solute may be at least one of a homogenous material and a heterogeneous material. Non-limiting examples of homogenous materials include inorganic materials (e.g., water soluble minerals, water soluble compounds such as salts), organic materials (e.g., pharmaceuticals, plasticizers, solvents, industrial chemicals, and organics found in produced water), and inorganic/organic hybrid materials (e.g., coordination complexes, and organometallic complexes such as dimethyl mercury). Non-limiting examples of heterogeneous materials include algae, microbes, small particulate matter, undissolved sewage material, nanoparticles, polymers, and food product solution materials, such as fruit juices. As used herein, the term "solution" means and includes a solution of the at least one solute in the water, a suspension of the at least one solute in the water, an emulsion of the at least one solute in the water, or combinations thereof. Since a person of ordinary skill in the art will recognize whether a particular reference describes a solution, a suspension, an emulsion or a combination thereof from the context, for the purposes of readability and claiming the invention, the term "solution" means a solution, a suspension, an emulsion, or a combination thereof. The at least one solute may, undesirably, be present in the aqueous feed liquid 118 as a contaminant or impurity of the water (e.g, where it is desired to purify or concentrate the water of the aqueous feed liquid 118). Alternatively, the water may be present in the aqueous feed liquid 118 as a contaminant or impurity of the solute (e.g., where it is desired to purify or concentrate the at least one solute of the aqueous feed liquid 118). The aqueous feed liquid 118 may be an aqueous liquid stream in which a dilute solution of the solute is available, but a concentrated solution of the solute is commercially desired. By way of non-limiting example, the aqueous feed liquid 118 may include an aqueous saline solution, ocean water, brine, brackish water, mineralized water, industrial waste water, produced water, mining waste (e.g., a potash solution, a lithium salt solution), a food product solution (e.g., a fruit juice solution, milk solution), an acid solution, a base solution, a synthetic fermentation broth, algal growth media, a microbial solution, landfill leachate, a radioactive material solution, a toxic material solution, or combinations thereof. In at least some embodiments, the aqueous feed liquid 118 includes ocean water.

The draw solution 122 may include water and a draw solute including at least one of the phosphazene compound and the triazine compound described above. In at least some embodiments, the draw solute is at least one of sodium hexa(4-carboxylatophenoxy)cyclotriphosphazene salt and sodium 2,4,6-tris(iminodiacetic acid)-1,3,5-triazine salt.

The at least one of the phosphazene compound and the triazine compound may at least partially dissociate in water to produce a plurality of particles (e.g., ions). By way of non-limiting example, when combined with water, a phosphazene compound including six salt functional groups may at least partially dissociate into from about three ions per molecule of phosphazene compound to about seven ions per molecule of phosphazene compound, such as from about 3.4 ions per molecule of phosphazene compound to about 3.7 ions per molecule of phosphazene compound, as measured by osmometry. Similarly, when combined with water, a triazine compound including six salt functional groups may at least partially dissociate into from about three ions to about seven ions. The at least partial dissociation of the at least one of the phosphazene compound and the triazine compound may enable a total number of particles (e.g., ions) per unit volume in the draw solution 122 to be greater than a total number of particles in the aqueous feed liquid 118. The difference between the total number of particles in the draw solution 122 and the total number of particles in the aqueous feed liquid 118, per unit volume, creates an osmotic pressure differential across the semi-permeable membrane 116 to draw the water of the aqueous feed liquid 118 toward the draw solution 122 by forward osmosis (i.e., the general tendency of water to move from an environment including less particles to an environment including more particles). The draw solution 122 may include any concentration of the at least one of the phosphazene compound and the triazine compound to achieve the relatively greater total number of particles in the draw solution 122 described above. The concentration of the at least one of the phosphazene compound and the triazine compound in the draw solution 122 may be controlled as desired by adjusting at least one of an amount of the water in the draw solution 122 and an amount of the at least one of the phosphazene compound and the triazine compound in the draw solution 122.

While FIG. 1 shows the aqueous feed liquid 118 and the draw solution 122 as being flowed or passed through the forward osmosis device 110 in opposite directions (i.e., countercurrent flow), the aqueous feed liquid 118 and the draw solution 122 may, alternatively, be flowed or passed through the forward osmosis device 110 in the same direction (i.e., concurrent flow), or at least one of the aqueous feed liquid 118 and the draw solution 122 may be substantially stagnant within the forward osmosis device 110. In at least one embodiment, the aqueous feed liquid 118 and the draw solution 122 are flowed through the forward osmosis device 110 in opposite directions.

As the water of the aqueous feed liquid 118 is drawn toward the draw solution 122, at least a portion of the water may osmose or diffuse through the semi-permeable membrane 116 to form a solute concentrate 120 in the first chamber 112 and a diluted draw solution 124 in the second chamber 114, where the diluted draw solution 124 includes the draw solute and the at least a portion of the water of the aqueous feed liquid 118. The semi-permeable membrane 116 may be any conventional membrane configured to facilitate the diffusion of water from the first chamber 112 into the second chamber 114, while substantially preventing the diffusion or passage of the at least one solute from the first chamber 112 into the second chamber 114. The semi-permeable membrane 116 may also substantially prevent the diffusion or passage of the at least one of the phosphazene compound and the triazine compound from the second chamber 114 into the first chamber 112. Suitable semi-permeable membranes 116 are commercially available from numerous sources including, but not limited to, Hydration Technology Innovations (Scottsdale, Ariz.) and included in products sold under the HYDROPACK®, LIFEPACK™, SEAPACK®, HYDROWELL®, EXPEDITION®, and X-PACK™ tradenames. The solute concentrate 120 may be disposed of or utilized as desired. The diluted draw solution 124 may be further processed, as described below.

The diluted draw solution 124 may be directed into a first chamber 128 of the filtration device 126. The first chamber 128 may be separated from a second chamber 130 by a semi-permeable membrane 132. The second chamber 130 may, initially, be substantially empty. The semi-permeable membrane 132 may be any conventional membrane configured to facilitate a pressure assisted diffusion of the water of the diluted draw solution 124 from the first chamber 128 into the second chamber 130 of the filtration device 126, while substantially preventing diffusion or passage of the at least one of the phosphazene compound and the triazine compound from the first chamber 128 into the second chamber 130 of the filtration device 126. By way of non-limiting example, the semi-permeable membrane 132 may include at least one of a microfiltration membrane, an ultrafiltration membrane, a nanofiltration membrane, and a reverse osmosis membrane, all of which are commercially available from numerous sources, such as from Hydration Technology Innovations (Scottsdale, Ariz.). In at least some embodiments, the semi-permeable membrane 132 includes a nanofiltration membrane.

Pressure may be applied to the diluted draw solution 124 within the first chamber 128 of the filtration device 126 to force at least a portion of the water of the diluted draw solution 124 through the semi-permeable membrane 132 and into the second chamber 130 to form a purified water product 134. A draw solution concentrate 122 including the at least one of the phosphazene compound and the triazine compound may be directed or recycled into the second chamber 114 of the forward osmosis device 110 for use in repeating the process described above.

While the combination of FIG. 1 illustrates producing the purified water product 134 through pressure-assisted filtration, the purified water product 134 may be produced through any conventional methods or techniques configured to separate the at least one of the phosphazene compound and the triazine compound of the diluted draw solution 124 from the water thereof. By way of non-limiting example, the purified water product 134 may be produced by subjecting the diluted draw solution 124 to at least one of adsorption, distillation, electrodialysis, and evaporation.

The phosphazene compound and the triazine compound disclosed herein are advantageous as compared to conventional draws solutes (e.g., $MgCl_2$, $CaCl_2$, NaCl, KCl, sucrose, $MgSO_4$, $KNO_3$) at least because the phosphazene compound and the triazine compound each enable a more energy efficient and less costly method and system of aqueous liquid treatment for the purification or concentration of at least one of water and a solute. For example, during forward osmosis, a conventional draw solute may back-diffuse through the forward osmosis (i.e., semi-permeable) membrane, resulting in additional costs to replace the conventional draw solute that is lost. Further, conventional draw solutes may require energy intensive processes, such as reverse osmosis or distillation, to be removed from the water they draw. Conversely, the relatively larger size and greater molecular weight of the phosphazene compound and of the triazine compound may reduce or prevent back diffusion of each of the phosphazene compound and of the triazine compound through the forward osmosis membrane, and may facilitate the removal of each of the phosphazene compound and of the triazine compound from water using less energy intensive separation processes, such as microfiltration, ultrafiltration, and nanofiltration. In addition, use of the phosphazene compound and the triazine compound of the present disclosure reduce membrane fouling, which reduces the cost of the process. The phosphazene compound and the triazine compound of the present disclosure are also advantageous because the process of purifying water using these compounds as draw solutes is less sensitive to the quality and contents of the aqueous feed liquid.

The phosphazene compound and the triazine compound disclosed herein also have increased durability, and advantageously enable increased osmotic pressure as compared to many conventional draw solutes. For example, conventional draw solutes are typically non-ionic (e.g., sucrose), mono-valent (e.g., NaCl, KCl), or di-valent (e.g., $MgCl_2$, $CaCl_2$). Thus, the draw solutes either do not dissociate in solution (i.e., one molecule of draw solute yields one particle in solution) or they produce a limited number of dissociated particles in solution (e.g., a mono-valent molecule produces two particles (e.g., ions) in solution, one for each discrete ion therein). The osmotic pressure invoked by conventional draw solutes can, therefore, be limited as osmotic pressure depends on the number of particles in the solution. Conversely, when combined with water each of the phosphazene compound and the triazine compound disclosed herein may dissociate into a greater number of particles (e.g., from about three particles to about seven particles), enabling increased osmotic pressure, and correspondingly improved water flux across the membrane as compared to conventional draw solutes.

The following examples serve to explain embodiments of the present disclosure in more detail. These examples are not to be construed as being exhaustive or exclusive as to the scope of the disclosure.

EXAMPLES

Example 1: Synthesis and isolation of hexa(4-ethylcarboxylatophenoxy)cyclotriphosphazene To a three neck round bottom flask was added a mechanical stirrer, a nitrogen purge, and a condenser. The flask was charged with approximately 300 ml of anhydrous tetrahydrofuran (THF). Sodium hydride (7.5 g, 326 mmol) was added slowly, followed by 4-ethylcarboxylatophenol (57.3 g, 345 mmol) dissolved in anhydrous 1,4-dioxane (~300 ml). The resulting mixture reacted vigorously and was stirred for one hour to ensure completion. To this solution was added a solution of hexachlorocyclotriphosphazene (10 g, 29 mmol) in anhydrous 1,4-dioxane (50 ml). The reaction was heated to reflux and THF was removed using a Dean-Stark trap until the boiling mixture reached 85° C. The reaction mixture was stirred for 43 hours under a nitrogen purge. Reaction progress was monitored by P-31 Nuclear Magnetic Resonance (NMR) spectrometry. Isolation of the compound was accomplished by filtration of the cooled reaction solution, followed by solvent removal by rotary evaporation to yield a crude oil. This oil was then dissolved in a mixture of diethyl ether and THF (100 ml total volume). This mixture was then poured into hexane (~500 ml) upon which a white precipitate formed. The precipitate was collected by filtration and was dried under ambient conditions to yield 9.6 g of a white crystalline solid in 30% yield.

Example 2: Formation of hexa(4-carboxyphenoxy) cyclotriphosphazene from hexa(4-ethylcarboxylatophenoxy)cyclotriphosphazene In an oven dried 500 ml round bottom flask was added anhydrous THF (300 ml) and potassium tert-butoxide (16 g, 143 mmol). The resulting solution was cooled to 0° C. in a water ice bath. In a separate flask, hexa(4-ethylcarboxylatophenoxy)cyclotriphosphazene (3 g, 2.1 mmol) was dissolved in anhydrous THF (20 ml). The solution was added to the base solution and the resulting mixture was allowed to come to room temperature and was stirred overnight. After stirring, the resulting mixture was poured into water (~1 L) and the pH was adjusted to approximately 3 with concentrated hydrochloric acid where a fine white precipitate was observed to form. Centrifugation of the precipitation solution yielded 2.1 g of a fine white powder for an 80% yield.

Example 3: Formation of Sodium hexa(4-carboxylatophenoxy)cyclotriphosphazene from hexa(4-carboxyphenoxy)cyclotriphosphazene Neutralization of the acidic functionality of the product of Example 2 was performed carefully to ensure excess base was not added. A solution of sodium hydroxide was prepared and standardized against dry potassium hydrogen phthalate (KHP) to yield a concentration of 0.177 M Na. Using this solution, a sample of hexa(4-carboxyphenoxy)cyclotriphosphazene (5 g, 4 mmol) was neutralized by suspending the phosphazene in water (~20 ml). The base was added using a buret. To assure that no excess sodium hydroxide remained, dry hexa(4-carboxyphenoxy)cyclotriphosphazene (~100 mg) was added incrementally to a final pH of 8. Once complete, the water was removed by rotary evaporation to give sodium hexa(4-carboxylatophenoxy)cyclotriphosphazene as a white powder in quantitative yield.

Example 4: Synthesis and isolation of 2-chloro-4,6-bis(diethyliminodiacetate)-1,3,5-triazine To a 250 mL 3-neck round bottom flask was added 5.0 g (26.7 mmol) cyanuric chloride, 9.3 mL (53.4 mmol) diisopropylethylamine (DIPEA) and 150 mL anhydrous THF. After cooling the solution to 0° C., 9.6 g (53.4 mmol) diethyliminodiacetate was added. The reaction was allowed to warm to room temperature, and stirred for 20 hours. The solution was filtered and the solvent removed in vacuo. The solid was dissolved in $CH_2Cl_2$ (150 mL) and washed with a 2% HCl solution (150 mL). The $CH_2Cl_2$ layer was separated, dried with $MgSO_4$, and the solvent removed in vacuo.

Example 5: Formation of 2,4,6-tris(diethyliminodiacetate)-1,3,5-triazine from 2-chloro-4,6-bis(diethyliminodiacetate)-1,3,5-triazine To a 250 mL 3-neck round bottom flask was added 5.0 g (10.2 mmol) 2-chloro-4,6-bis(diethyliminodiacetate)-1,3,5-triazine, 7.1 mL (40.8 mmol) diisopropylethylamine (DIPEA), 7.7 g (40.8 mmol) diethyliminodiacetate, and 150 mL anhydrous 1,4-dioxane. The reaction was refluxed for 24 hours. The solution was filtered hot, and the solvent removed in vacuo. The yellow-orange liquid was dissolved in $CH_2Cl_2$ (150 mL) and washed with a 2% HCl solution (150 mL). The $CH_2Cl_2$ layer was separated, dried with $MgSO_4$, and the solvent removed in vacuo.

Example 6: Formation of 2,4,6-tris(iminodiacetic acid)-1,3,5-triazine from 2,4,6-tris(diethyliminodiacetate)-1,3,5-triazine To a 250 mL round bottom flask was added 5.0 g 2,4,6-tris(diethyliminodiacetate)-1,3,5-triazine, 100 mL 1,4-dioxane, 100 mL $H_2O$, and 10 mL conc. HCl. The reaction was refluxed for 6 hours. The solvent was removed in vacuo and the solid dried in a vacuum oven (60° C.) overnight.

Example 7: Formation of 2,4,6-tris(iminodiacetic acid)-1,3,5-triazine salt from 2,4,6-tris(iminodiacetic acid)-1,3,5-triazine To a 250 mL round bottom flask was added 5.0 g 2,4,6-tris(iminodiacetic acid)-1,3,5-triazine and 100 mL $H_2O$. Sodium hydroxide (1.3 M) was added until the pH was just above 7. The solvent was removed in vacuo and the solid dried in a vacuum oven (60° C.) overnight.

Figure 2:
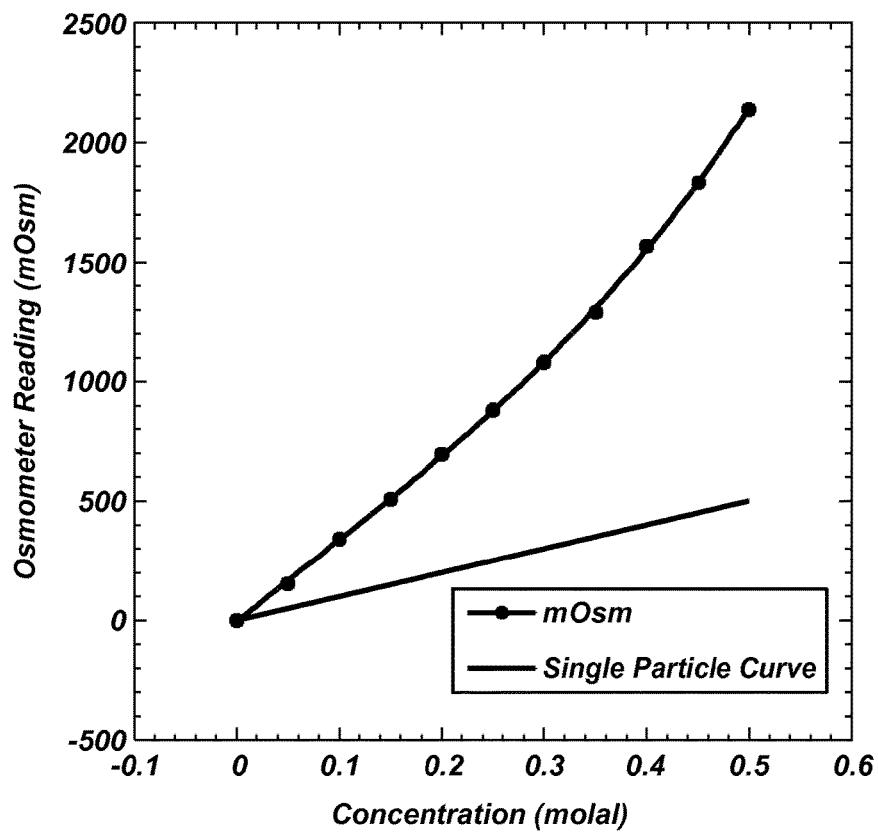
FIG. 2 is a graphical representation of the osmotic pressure of a phosphazene compound, as described in Example 8.

Example 8: Osmotic Pressure of Sodium Hexa(4-Carboxylatophenoxy)Cyclotriphosphazene Relative to a Solute Such as Sucrose The osmotic pressure of aqueous feed solutions having different concentrations of sodium hexa(4-carboxylatophenoxy)cyclotriphosphazene was compared against the osmotic pressure of aqueous solutions wherein one mole of solute in aqueous feed liquid corresponds to about one mole of particles (e.g., ions) in the aqueous feed liquid (e.g., aqueous solutions having different concentrations of sucrose corresponding to the concentrations of sodium hexa(4-carboxylatophenoxy)cyclotriphosphazene in the aqueous feed solutions). A graphical representation of the comparison is depicted in FIG. 2. As shown in FIG. 2, at the lowest tested sodium hexa(4-carboxylatophenoxy)cyclotriphosphazene concentration (i.e., 0.05 molal), one mole of sodium hexa(4-carboxylatophenoxy)cyclotriphosphazene exhibited an osmotic pressure corresponding to about 3.1 moles of particles (e.g., ions) in aqueous feed liquid. Further, at the highest tested sodium hexa(4-carboxylatophenoxy)cyclotriphosphazene concentration (i.e., 0.5 molal), one mole of sodium hexa(4-carboxylatophenoxy)cyclotriphosphazene exhibited an osmotic pressure corresponding to about 4.3 moles of particles (e.g., ions) in aqueous feed liquid. Table 1 below summarizes the osmotic pressure data for the various aqueous feed solutions depicted in FIG. 2.

TABLE 1

Osmotic pressure data for different aqueous sodium hexa(4-carboxylatophenoxy)cyclotriphosphazene solutions

| Solution molality | Osmometry reading (mOsm) |
|---|---|
| 0.0000 | 0.0000 |
| 0.050000 | 154.00 |
| 0.10000 | 342.00 |
| 0.15000 | 509.30 |
| 0.20000 | 695.70 |
| 0.25000 | 881.70 |
| 0.30000 | 1081.0 |
| 0.35000 | 1288.3 |
| 0.40000 | 1565.7 |

TABLE 1-continued

Osmotic pressure data for different aqueous sodium hexa(4-carboxylatophenoxy)cyclotriphosphazene solutions

| Solution molality | Osmometry reading (mOsm) |
|---|---|
| 0.45000 | 1835.0 |
| 0.50000 | 2140.0 |

Example 9: Osmotic Pressure of Sodium of 2,4,6-Tris(Iminodiacetic Acid)-1,3,5-Triazine Salt Relative to Sucrose The osmotic pressure of an aqueous 0.2 molal 2,4,6-tris(iminodiacetic acid)-1,3,5-triazine salt solution was compared against the osmotic pressure of an aqueous 0.2 molal sucrose solution. The osmotic pressure of the 0.2 molal sucrose solution was determined by applying a quadratic fit to osmotic pressure measurements (i.e., expressed in terms of osmolality, Osm/kg) for aqueous sucrose solutions having sucrose concentrations between 0 molal and 1.5 molal. The aqueous 0.2 molal 2,4,6-tris(iminodiacetic acid)-1,3,5-triazine salt solution had an osmotic pressure of about 735 mOsm/kg, whereas the osmotic pressure of the aqueous 0.2 molal sucrose solution was interpolated to be about 205 mOsm/kg. One molecule of the 2,4,6-tris(iminodiacetic acid)-1,3,5-triazine salt in aqueous feed liquid was calculated to exhibit the osmotic pressure of about 3.4 particles (e.g., ions) in aqueous feed liquid.

Figure 3:
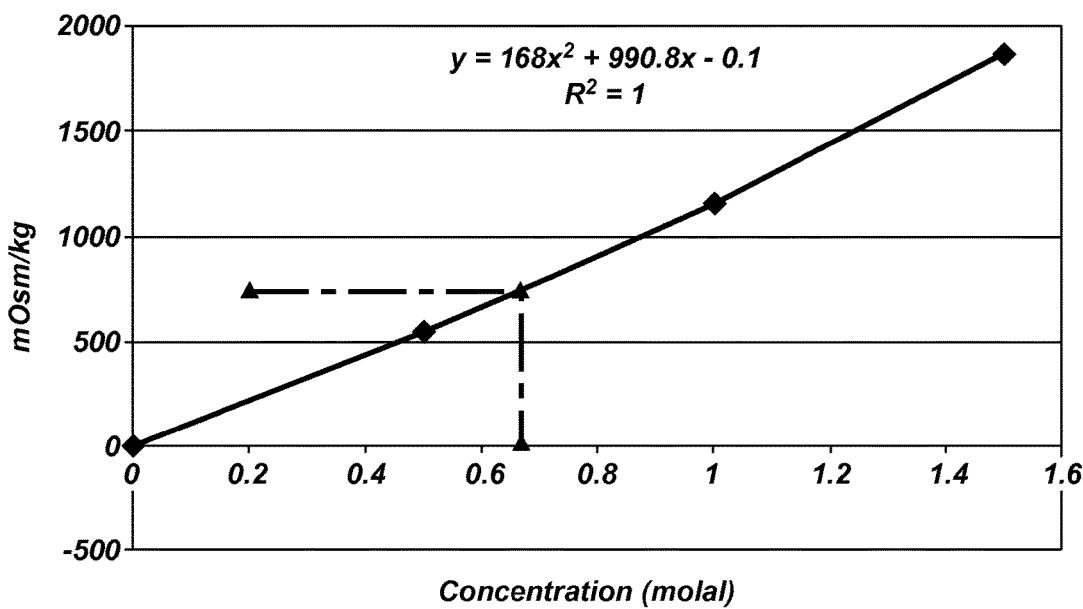
FIG. 3 is a graphical representation of the osmotic pressure of a triazine compound relative to sucrose, as described in Example 9.

A graphical representation of the osmotic pressure of an aqueous 0.2 molal 2,4,6-tris(iminodiacetic acid)-1,3,5-triazine salt solution as compared to aqueous sucrose solutions at different sucrose concentrations is shown in FIG. 3. In FIG. 3, the solid black line shows osmotic pressure as a function of molal concentration of sucrose in an aqueous sucrose solution. The triangular marking above the 0.2 gridline marking shows the osmotic pressure of the aqueous 0.2 molal 2,4,6-tris(iminodiacetic acid)-1,3,5-triazine salt solution (i.e., about 735 mOsm/kg). The horizontal dash line and the vertical dashed line are provided to show the molal concentration of sucrose for an aqueous sucrose solution imparting an osmotic pressure approximately equivalent to that of about a 0.2 molal 2,4,6-tris(iminodiacetic acid)-1,3,5-triazine salt solution. The horizontal dashed line and the vertical dashed line show that an aqueous 0.667 molal sucrose solution will yield an osmotic pressure of about 735 mOsm/kg.

Figure 4A:
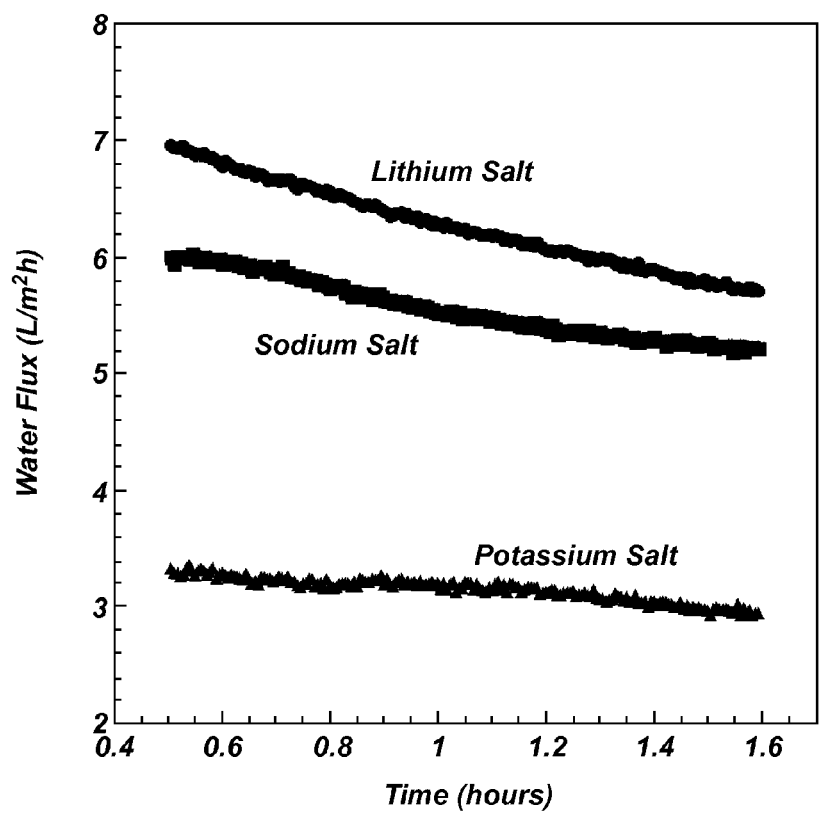
FIG. 4A is a graphical representation of water flux across semi-permeable membranes as a function of time using a phosphazene compound as a draw solute for different aqueous salt solutions, as described in Example 10.

Example 10: Water Flux Across a Semi-Permeable Membrane as a Function of Time and Temperature Using Sodium Hexa(4-Carboxylatophenoxy)Cyclotriphosphazene An aqueous sodium salt solution, an aqueous lithium salts solution, and an aqueous potassium salt solution were separately provided on first sides of HTI cartridge membranes (model 081118-2), with aqueous draw solutions having an initial concentration of 0.077M sodium hexa(4-carboxylatophenoxy)cyclotriphosphazene provided on second sides of the HTI cartridge membranes. The temperature at the HTI cartridge membranes was 29° C. An osmotic pressure differential across each of the HTI cartridge membranes generated a flow of water from the first side of each of the membranes, across each of the membranes, and to the second side of each of the membranes. A graphical representation of the water flux across the HTI cartridge membranes for each of the aqueous sodium salt solution, the aqueous lithium salt solution, and the aqueous potassium salt solution over approximately a one and a half hour period is shown in FIG. 4A. No sodium hexa(4-carboxylatophenoxy)cyclotriphosphazene was found to have back diffused through the HTI cartridge membranes.

Figure 4B:
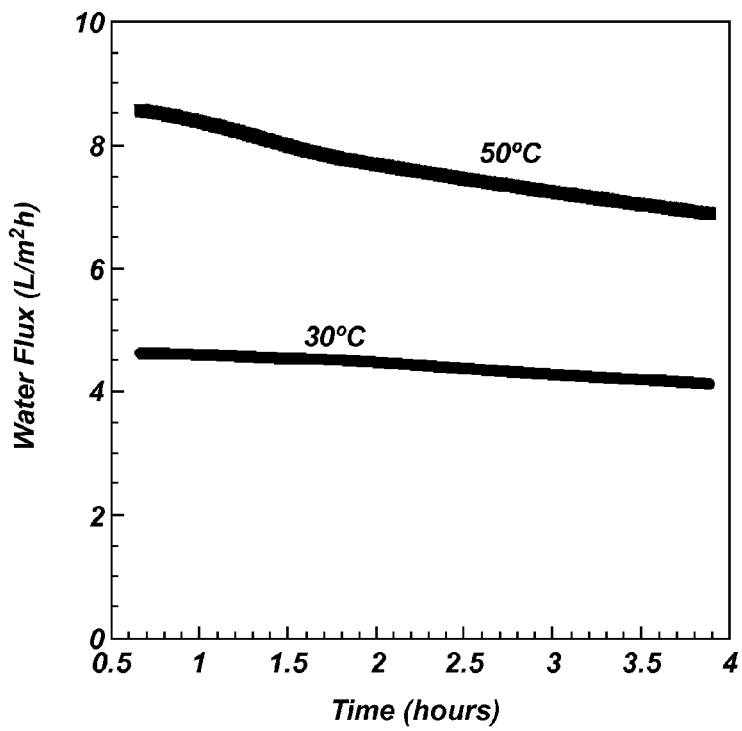
FIG. 4B is a graphical representation of water flux across semi-permeable membranes as a function of time and temperature using a phosphazene compound as a draw solute for an aqueous salt solution, as described in Example 10.

In addition, a first aqueous sodium salt solution and a second aqueous sodium salt solution were separately provided on first sides of HTI cartridge membranes (model 081118-2), with aqueous draw solutions including having an initial concentration of 0.077M sodium hexa(4-carboxylatophenoxy)cyclotriphosphazene provided on second sides of the HTI cartridge membranes. The temperature at one HTI cartridge membrane was 30° C. The temperature at another HTI cartridge membrane was 50° C. A graphical representation of the water flux across the HTI cartridge membranes for each of the first aqueous sodium salt solution and a second aqueous sodium salt solution over approximately a four hour period is shown in FIG. 4B.

Figure 5:
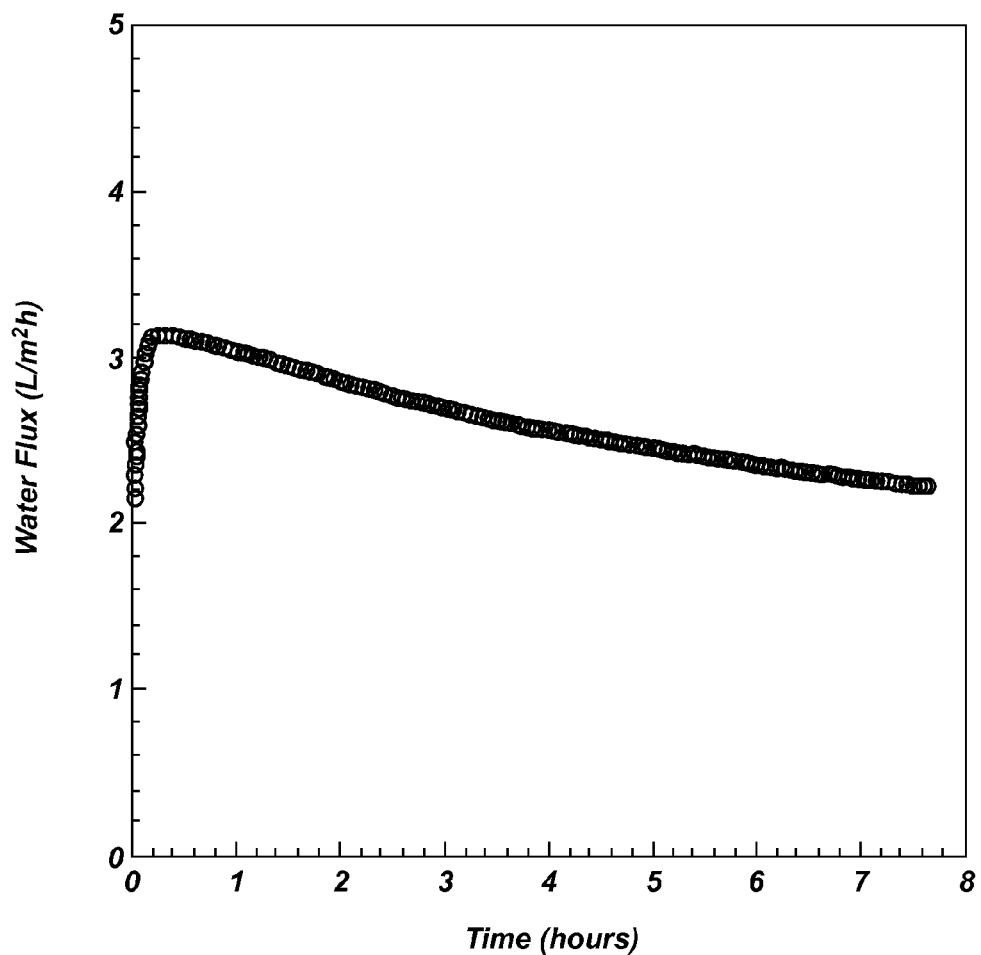
FIG. 5 is a graphical representation of water flux across a semi-permeable membrane as a function of time using a triazine compound as a draw solute for an aqueous salt solution, as described in Example 11.

Example 11: Water Flux Across a Semi-Permeable Membrane as a Function of Time Using Sodium 2,4,6-Tris(Iminodiacetic Acid)-1,3,5-Triazine An aqueous feed liquid including sodium salt was provided on a first side of an HTI cartridge membrane, with an aqueous draw solution including a 0.142 M concentration of sodium 2,4,6-tris(iminodiacetic acid)-1,3,5-triazine on a second side of the HTI cartridge membrane (model 081118-1). The temperature at the HTI cartridge membrane was 29° C. An osmotic pressure differential across the HTI cartridge membrane generated a flow of water from the first side of the membrane, across the HTI cartridge membrane, and to the second side of the membrane. After seven hours, the aqueous draw solution had a sodium 2,4,6-tris(iminodiacetic acid)-1,3,5-triazine concentration of 0.074 M. The flux and the draw solution concentration data is summarized below in Table 2. No sodium 2,4,6-tris(iminodiacetic acid)-1,3,5-triazine was found to have back diffused through the HTI cartridge membrane. A graphical representation of the flux of the water across the HTI cartridge membrane over the seven hour period is shown in FIG. 5.

TABLE 2

Performance data for sodium 2,4,6-tris(iminodiacetic acid)-1,3,5-triazine

| Operating Time (hours) | Flux (L/m²h) | Draw Solution Concentration (M) |
|---|---|---|
| Initial | — | 0.1419 |
| 1 | 3.024 | 0.1208 |
| 2 | 2.852 | 0.1067 |
| 3 | 2.690 | 0.0967 |
| 4 | 2.557 | 0.0891 |
| 5 | 2.452 | 0.0830 |
| 6 | 2.356 | 0.0781 |
| 7 | 2.271 | 0.0739 |

Figure 6A:
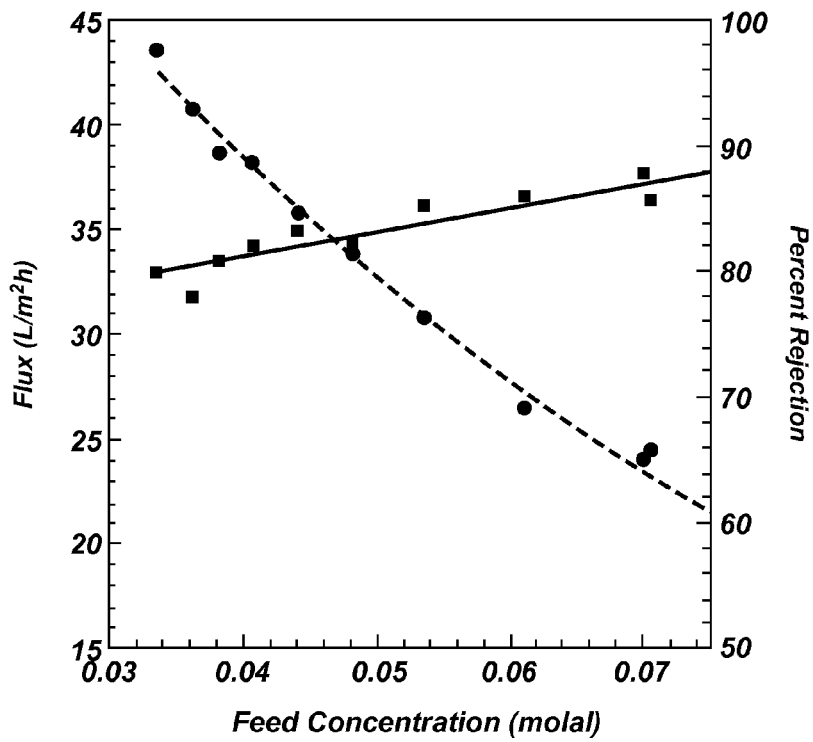
FIGS. 6A through 6D are graphical representations of water flux across and percent phosphazene compound rejection by nanofiltration membranes as a function of phosphazene compound concentration in aqueous solutions, as described in Example 12.
Figure 6B:
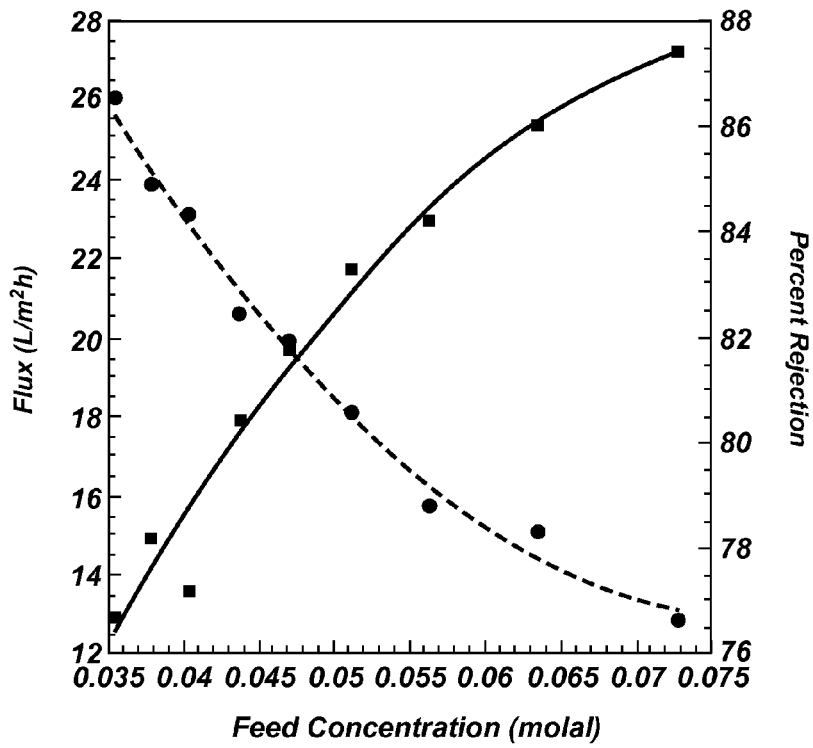
Figure 6C:
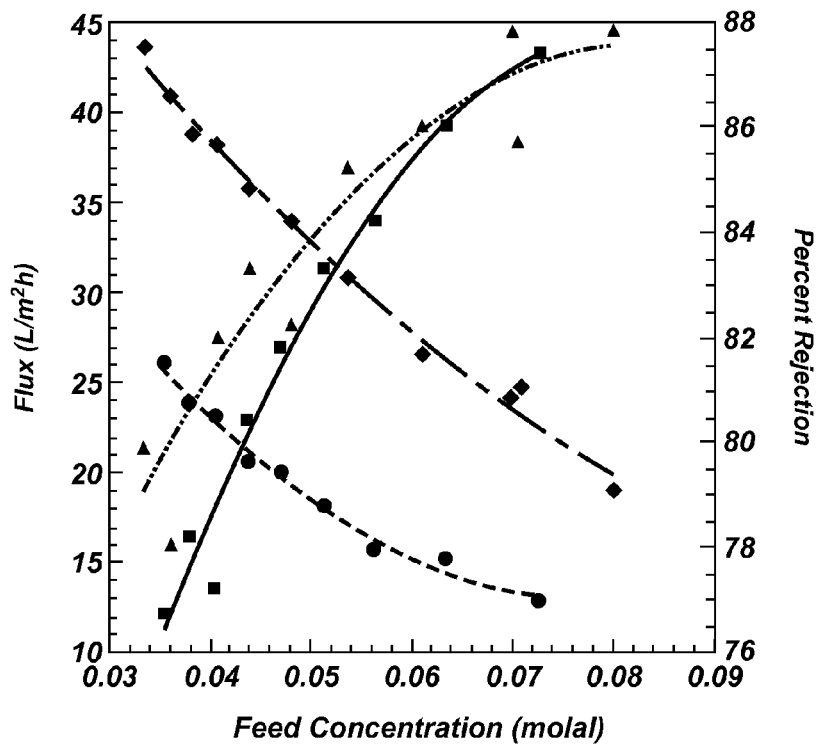

Example 12: Water Extraction from Solutions Including Sodium Hexa(4-Carboxylatophenoxy)Cyclotriphosphazene Sodium hexa(4-carboxylatophenoxy)cyclotriphosphazene was added to deionized water and mixed to form two homogenous solutions. Each solution and was filtered through an Applied Membranes model M-N1812A5 nanofiltration membrane (5 ft², 50% rejection NaCl). The first solution was filtered at an initial purified water production rate or initial water flux of about 690 milliliters per minute (ml/min). The second solution was filtered at an initial water flux of about 300 ml/min. FIGS. 6A and 6B are graphical representations of water flux and percent sodium hexa(4-carboxylatophenoxy)cyclotriphosphazene rejection as a function of sodium hexa(4-carboxylatophenoxy)cyclotriphosphazene concentration for the first solution and the second solution, respectively. In each of FIGS. 6A and 6B, the trendline defined by filled circles (●) represents water flux across the nanofiltration membrane, and the trendline defined by filled squares (■) represents percent sodium hexa(4-carboxylatophenoxy)cyclotriphosphazene rejection by the nanofiltration membrane. FIG. 6C is a graphical representation comparing the results depicted in FIGS. 6A and 6B. In FIG. 6C, the trendlines defined by filled diamonds (♦) and filled triangles (▲) respectively represent water flux and percent sodium hexa(4-carboxylatophenoxy) cyclotriphosphazene rejection for the first solution, and the trendlines defined by filled circles (●) and filled squares (■) respectively represent water flux and percent sodium hexa (4-carboxylatophenoxy)cyclotriphosphazene rejection for the second solution. FIGS. 6A through 6C illustrate that purified water was extracted from the solutions with a percent sodium hexa(4-carboxylatophenoxy)cyclotriphosphazene rejection within a range of from about 76 percent to about 93 percent, depending on water flux. In addition, as shown in FIGS. 6A through 6C, decreasing water flux (e.g., from about 690 ml/min for the first solution to about 300 ml/min for the second solution) facilitated lower flux against sodium hexa(4-carboxylatophenoxy) cyclotriphosphazene with comparable sodium hexa(4-carboxylatophenoxy)cyclotriphosphazene rejection. Subsequent filtration of pure water across the nanofiltration membranes used to filter the first solution and the second solution indicated that the use of sodium hexa(4-carboxylatophenoxy)cyclotriphosphazene resulted in minimal to no irreversible fouling of the nanofiltration membranes.

Figure 6D:
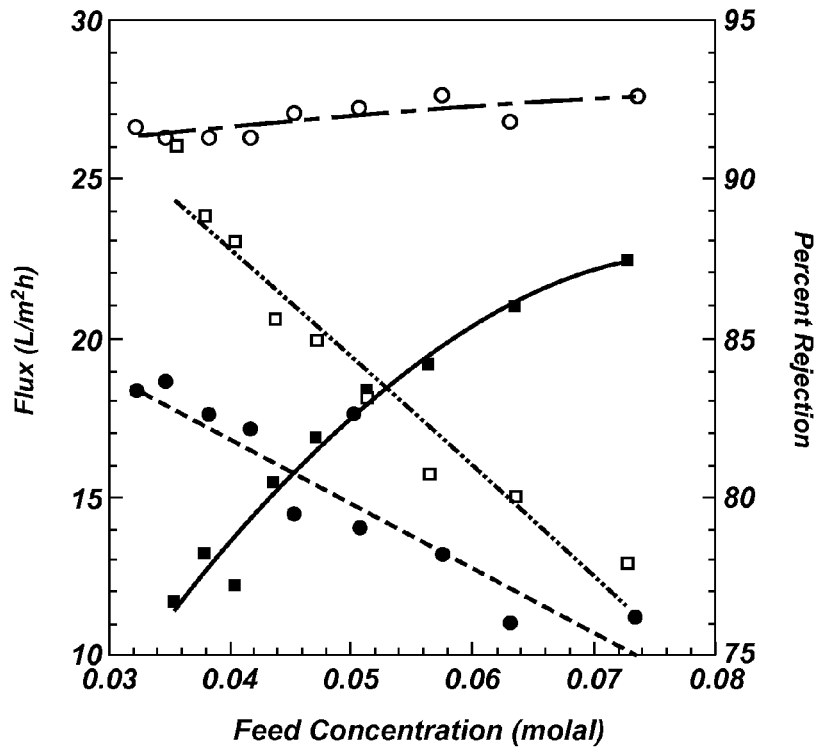

Next, sodium hexa(4-carboxylatophenoxy)cyclotriphosphazene was added to deionized water and mixed to again form two homogenous solutions. One solution and was filtered through an Applied Membranes model M-N1812A5 nanofiltration membrane (5 ft², 50% rejection NaCl), and the other solution was filtered through an Applied Membranes model M-N1812A9 nanofiltration membrane (5 ft², 90% rejection NaCl). FIG. 6D is a graphical representation of water flux and percent sodium hexa(4-carboxylatophenoxy) cyclotriphosphazene rejection as a function of sodium hexa (4-carboxylatophenoxy)cyclotriphosphazene concentration for each of the solutions. In FIG. 6D, the trendlines defined by empty squares (□) and filled squares (■) respectively represent water flux and percent sodium hexa(4-carboxylatophenoxy) cyclotriphosphazene rejection for the solution filtered by the model M-N1812A5 nanofiltration membrane, and the trendlines defined by filled circles (●) and empty circles (○) respectively represent water flux and percent sodium hexa(4-carboxylatophenoxy)cyclotriphosphazene rejection for the solution filtered by the model M-N1812A9 nanofiltration membrane. Subsequent filtration of pure water across the nanofiltration membranes used to filter the solutions indicated that the use of sodium hexa(4-carboxylatophenoxy)cyclotriphosphazene resulted in minimal to no irreversible fouling of the nanofiltration membranes.

While the present disclosure may be susceptible to various modifications and alternative forms, specific embodiments have been shown by way of example in the drawings and have been described in detail herein. However, it should be understood that the present disclosure is not intended to be limited to the particular forms disclosed. Rather, the present disclosure includes all modifications, equivalents, and alternatives falling within the scope of the present disclosure as defined by the following appended claims and their legal equivalents.

What is claimed is:

1. A method of treating an aqueous liquid, the method comprising:
    delivering an aqueous feed liquid comprising water and at least one solute to a first side of a membrane;
    delivering a draw solution comprising water and a draw solute comprising one or more of a phosphazene compound and a triazine compound to a second side of the membrane;
    osmosing at least a portion of the water of the aqueous feed liquid across the membrane and into the draw solution to form a diluted draw solution comprising water and the draw solute; and
    separating the water of the diluted draw solution from the draw solute of the diluted draw solution to form a purified water product.

2. The method of claim 1, wherein delivering the aqueous feed liquid comprises delivering at least one of an aqueous saline solution, ocean water, brine, brackish water, mineralized water, and industrial waste water.

3. The method of claim 1, wherein delivering a draw solution comprises selecting the draw solute of the draw solution to comprise a cyclic phosphazene compound having a plurality of salt-terminated pendant groups bonded to phosphorus atoms of a plurality of phosphorus-nitrogen units.

4. The method of claim 1, wherein delivering a draw solution comprises selecting the draw solute of the draw solution to comprise a triazine compound having a plurality of salt-terminated pendant groups bonded to carbon atoms of a triazine ring.

5. The method of claim 1, wherein delivering a draw solution comprises selecting the draw solute to at least partially dissociate in water to produce from about three particles of the draw solute to about seven particles of the draw solute.

6. The method of claim 1, wherein delivering a draw solution further comprises adjusting at least one of an amount of the water in the draw solution and an amount of the draw solute in the draw solution such that the draw solution comprises a greater number of particles than a total number of particles in the aqueous feed liquid.

7. The method of claim 1, wherein separating the water of the diluted draw solution from the draw solute of the diluted draw solution comprises filtering the diluted draw solution.

8. The method of claim 7, wherein filtering the diluted draw solution comprises subjecting the diluted draw solution to at least one of microfiltration, ultrafiltration, and nanofiltration.

9. A method of treating an aqueous liquid, the method comprising:
    delivering an aqueous feed liquid comprising water and one or more of a homogenous material and a heterogeneous material to a first side of a semi-permeable membrane;
    delivering a draw solution comprising water and at least one draw solute comprising one or more of at least one cyclic phosphazene compound and at least one triazine compound to a second side of the semi-permeable membrane;

drawing at least a portion of the water of the aqueous feed liquid across the semi-permeable membrane and into the draw solution to form a diluted draw solution comprising water and the at least one draw solute; and separating the water of the diluted draw solution from the at least one draw solute of the diluted draw solution to form a purified water product.

10. The method of claim 9, wherein delivering a draw solution comprises selecting the at least one draw solute of the draw solution to comprise one or more compounds independently having one of the following chemical structures:

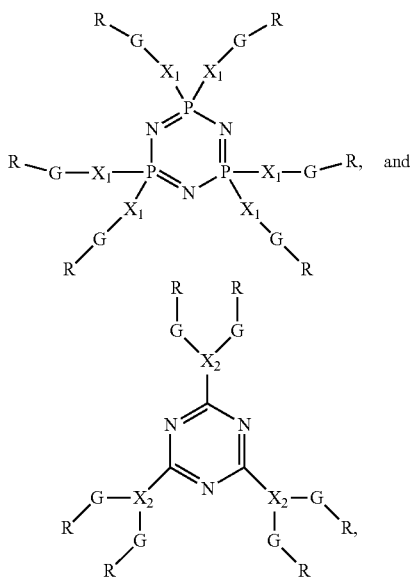

where each $X_1$ is independently —O—, —S—, or —NH—;

each $X_2$ is independently —N—, —P—, —CH—, or —SiH—;

each G is independently an alkylene group, an alkenylene group, an alkynylene group, an alicyclic group, an arylene group, —CO—, —SO$_2$—, —SO—, —PO—, —O—, —S—, or —NH—; and each R is independently a sulfonate salt group, a phosphonate salt group, a quaternary ammonium salt group, or a quaternary phosphorous salt group.

11. The method of claim 10, wherein each R is independently one of the following structures:

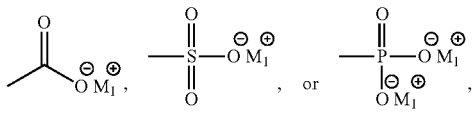

where each $M_1$ is independently a mono-valent cationic counterion or a multi-valent cationic counterion.

12. The method of claim 11, wherein each $M_1$ is independently Li$^+$, Na$^+$, K$^+$, NH$_4^+$, Ca$_2^+$, Mg$_2^+$, Zn$^{2+}$, (R$_1$)$_4$N$^+$, or (R$_1$)$_4$P$^+$, wherein each R is independently H, a substituted alkyl group having from 1 carbon atom to 8 carbon atoms, an unsubstituted alkyl group having from 1 carbon atom to 8 carbon atoms, a substituted aryl group having from 5 carbon atoms to 8 carbon atoms, or an unsubstituted aryl group having from 5 carbon atoms to 8 carbon atoms.

13. The method of claim 10, wherein each R is independently one of the following structures:

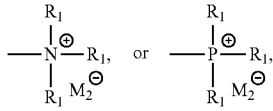

where each $R_1$ is independently H, a substituted alkyl group having from 1 carbon atom to 8 carbon atoms, an unsubstituted alkyl group having from 1 carbon atom to 8 carbon atoms, a substituted aryl group having from 5 carbon atoms to 8 carbon atoms, or an unsubstituted aryl group having from 5 carbon atoms to 8 carbon atoms; and each $M_2$ is independently a mono-valent anionic counterion or a multi-valent anionic counterion.

* * * * *

UNITED STATES PATENT AND TRADEMARK OFFICE
CERTIFICATE OF CORRECTION

PATENT NO. : 10,099,178 B2
APPLICATION NO. : 14/948019
DATED : October 16, 2018
INVENTOR(S) : Frederick F. Stewart et al.

Page 1 of 1

It is certified that error appears in the above-identified patent and that said Letters Patent is hereby corrected as shown below:

In the Specification

| | | |
|---|---|---|
| Column 1, | Line 8, | change "May 24, 2012 now" to --May 24, 2012, now-- |
| Column 6, | Line 29, | change "sodium (NO, or" to --sodium ($Na^+$, or-- |
| Column 6, | Line 59, | change "or iodine (F);" to --or iodine ($I^-$);-- |
| Column 27, | Line 35, | change "draw solution concentrate 122" to --draw solution 122 concentrate-- |

Signed and Sealed this
Twenty-first Day of May, 2019

Andrei Iancu
*Director of the United States Patent and Trademark Office*